(12) United States Patent
Landis

(10) Patent No.: US 7,725,949 B2
(45) Date of Patent: Jun. 1, 2010

(54) VENTILATED FACE SHIELD ASSEMBLY WITH GLARE SHIELD

(75) Inventor: Timothy J. Landis, Granite Bay, CA (US)

(73) Assignee: OP-D-OP, Inc., Roseville, CA (US)

( * ) Notice: Subject to any disclaimer, the term of this patent is extended or adjusted under 35 U.S.C. 154(b) by 1453 days.

(21) Appl. No.: 11/101,190

(22) Filed: Apr. 6, 2005

(65) Prior Publication Data

US 2005/0251890 A1 Nov. 17, 2005

Related U.S. Application Data

(60) Provisional application No. 60/560,801, filed on Apr. 7, 2004, provisional application No. 60/578,625, filed on Jun. 9, 2004.

(51) Int. Cl.
*A41B 13/00* (2006.01)
(52) U.S. Cl. .................................................. 2/9; 2/206
(58) Field of Classification Search ........................ 2/9, 2/427, 15, 11, 12, 206, 432, 429, 436; 128/857, 128/858
See application file for complete search history.

(56) References Cited

U.S. PATENT DOCUMENTS

| | | | | |
|---|---|---|---|---|
| 2,638,593 A | * | 5/1953 | Eloranta | 2/12 |
| 2,881,443 A | * | 4/1959 | Barker, Jr. | 2/9 |
| 3,214,767 A | * | 11/1965 | Weber | 2/9 |
| 4,852,186 A | | 8/1989 | Landis | |
| 4,856,109 A | * | 8/1989 | Desy et al. | 2/9 |
| 4,864,653 A | | 9/1989 | Landis | |
| 4,964,171 A | | 10/1990 | Landis | |
| 5,206,956 A | * | 5/1993 | Olson | 2/13 |
| 5,247,706 A | * | 9/1993 | Mark | 2/9 |
| D375,583 S | | 11/1996 | Landis | |
| 5,692,522 A | | 12/1997 | Landis | |
| 5,694,925 A | * | 12/1997 | Reese et al. | 128/206.19 |
| 6,016,808 A | | 1/2000 | Landis | |

* cited by examiner

*Primary Examiner*—Shaun R Hurley
*Assistant Examiner*—Andrew W Sutton
(74) *Attorney, Agent, or Firm*—John P. O'Banion

(57) ABSTRACT

A ventilated face shield assembly with a glare shield which protects the face of the wearer from debris and/or hazardous materials, such as biological materials, and is particularly well suited for medical and dental applications. A ventilated headband is used as a spacer and to support the face shield assembly on the face of the wearer. The glare shield and face shield are made of sheet material and are configured for flat storage. In one embodiment, the glare shield and face shield are coupled with a hinge and a flexible cord retains the glare shield and face shield in an arcuate configuration. In another embodiment, a protective breathing mask is attached to the face shield assembly and supports the glare shield and face shield. In a further embodiment, the glare shield is used as the spacer for the face shield.

37 Claims, 20 Drawing Sheets

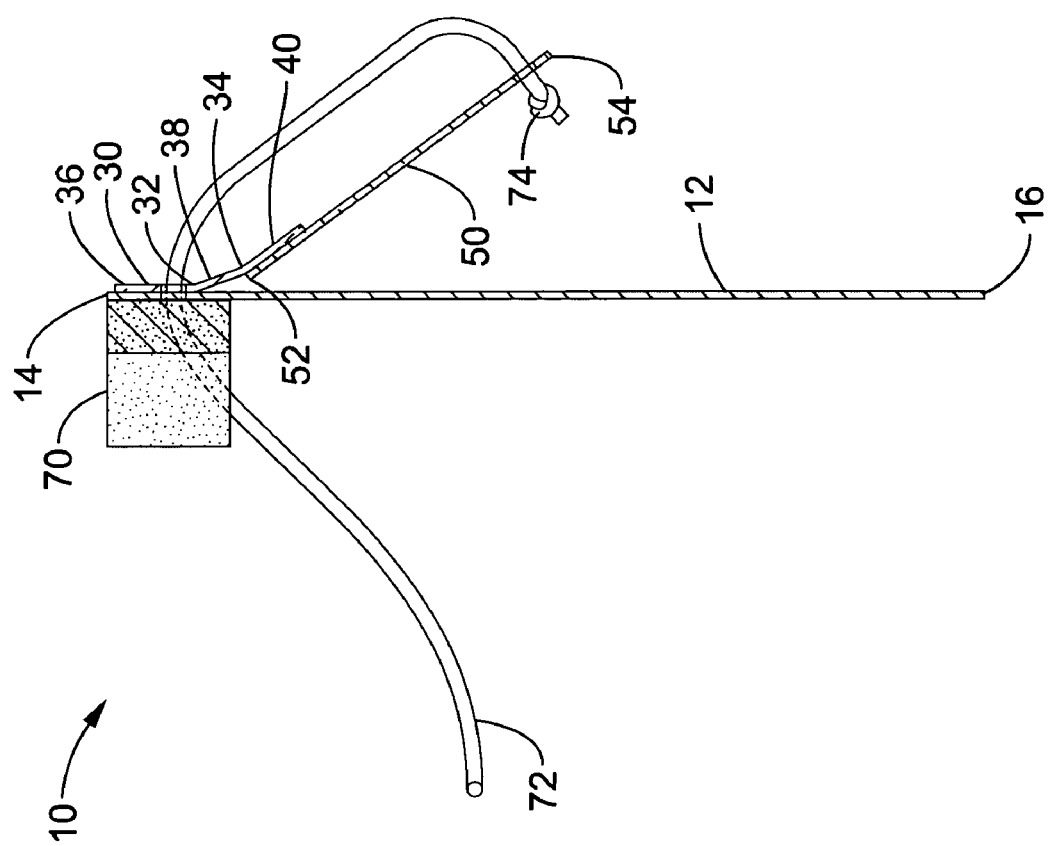

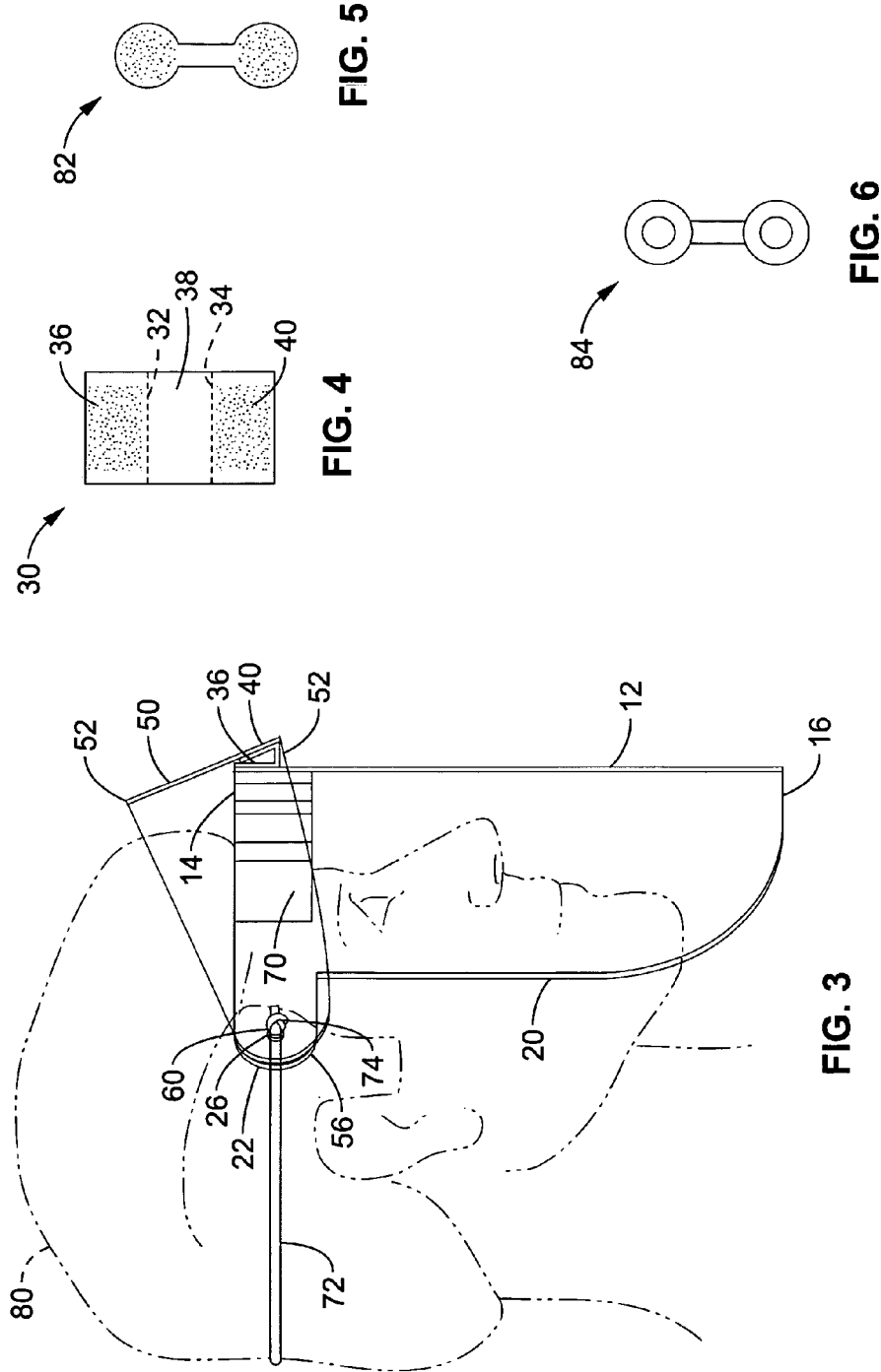

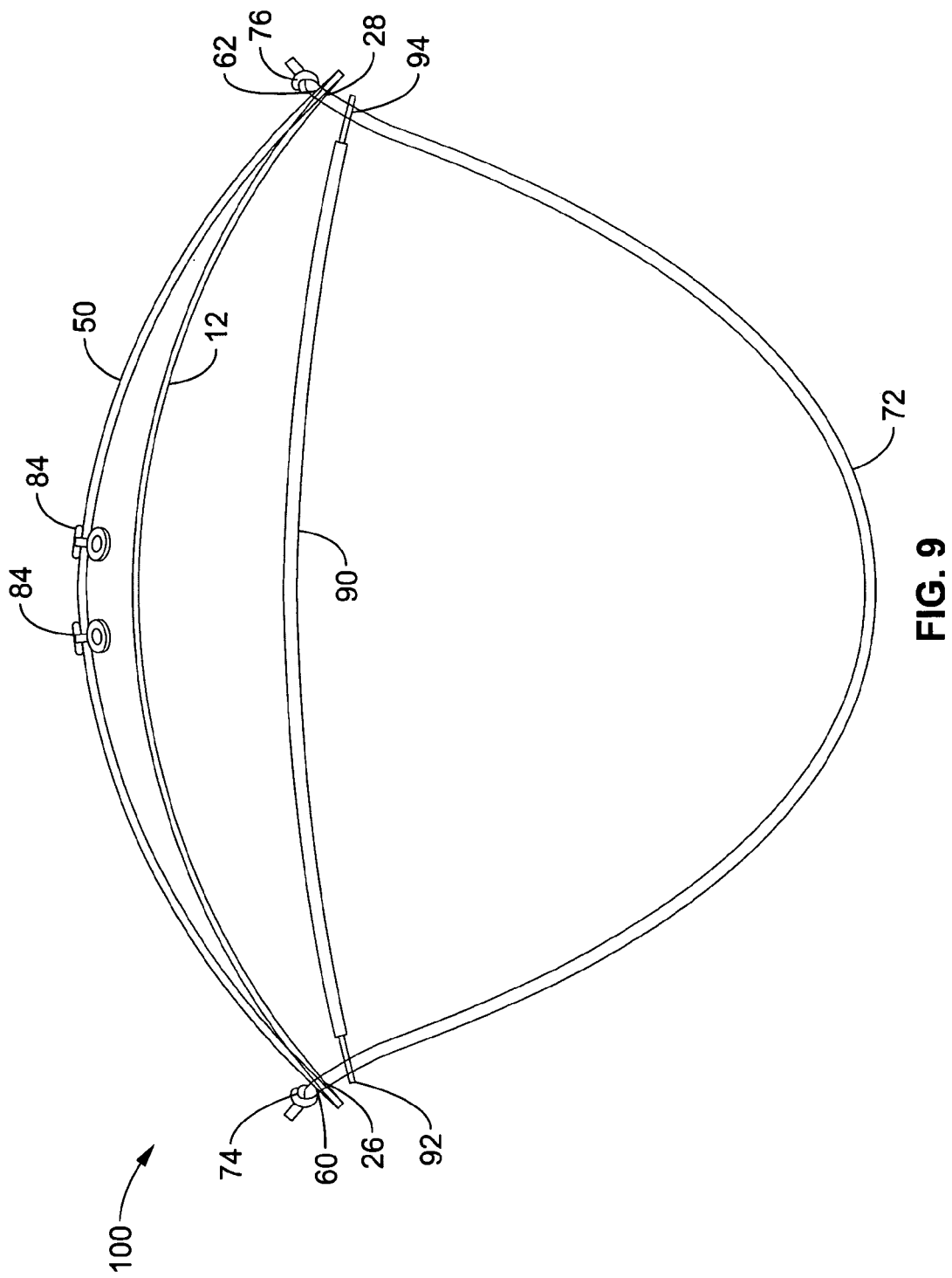

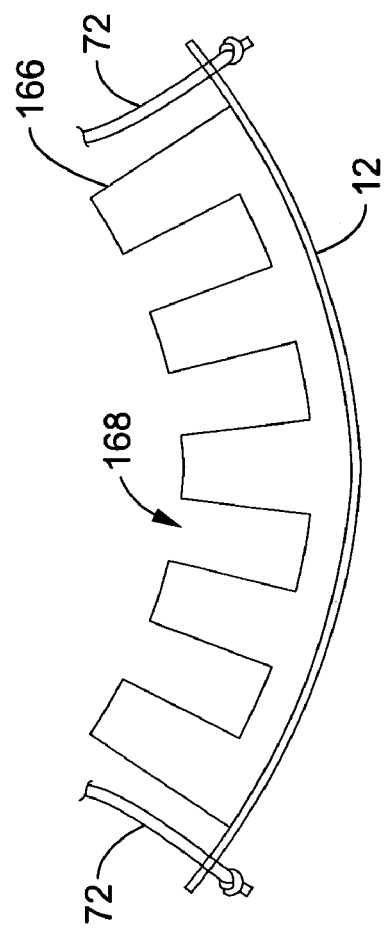
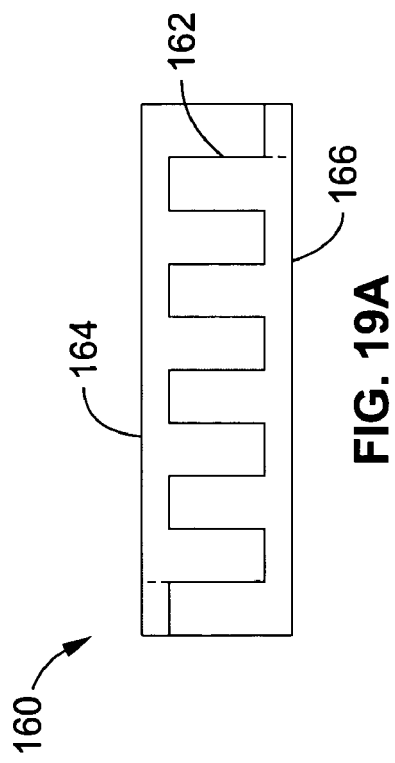
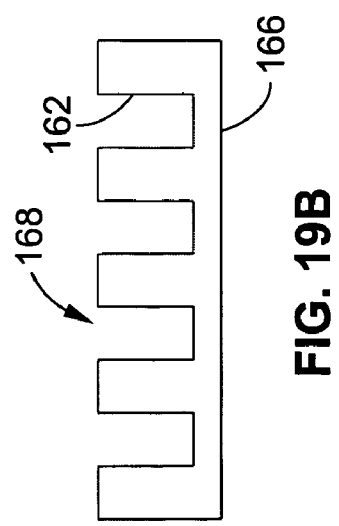
FIG. 19C
FIG. 19A
FIG. 19B

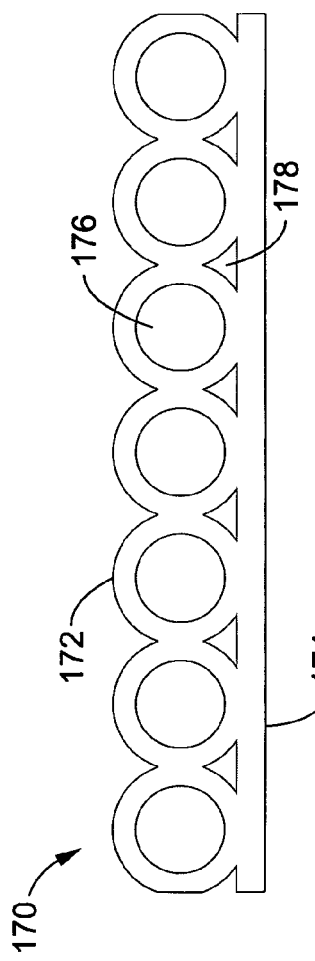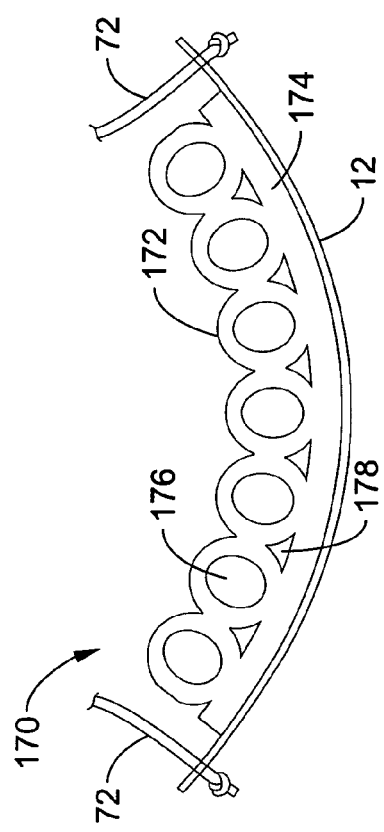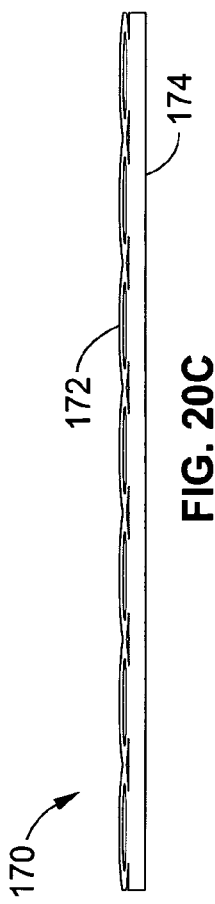
FIG. 20A
FIG. 20B
FIG. 20C

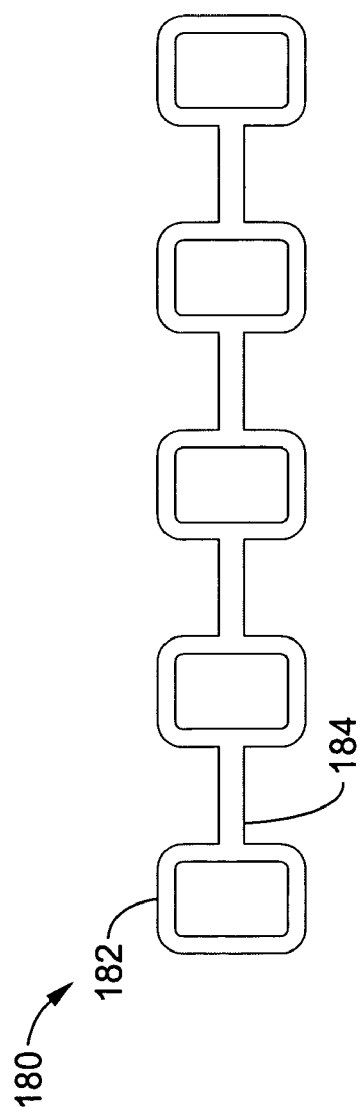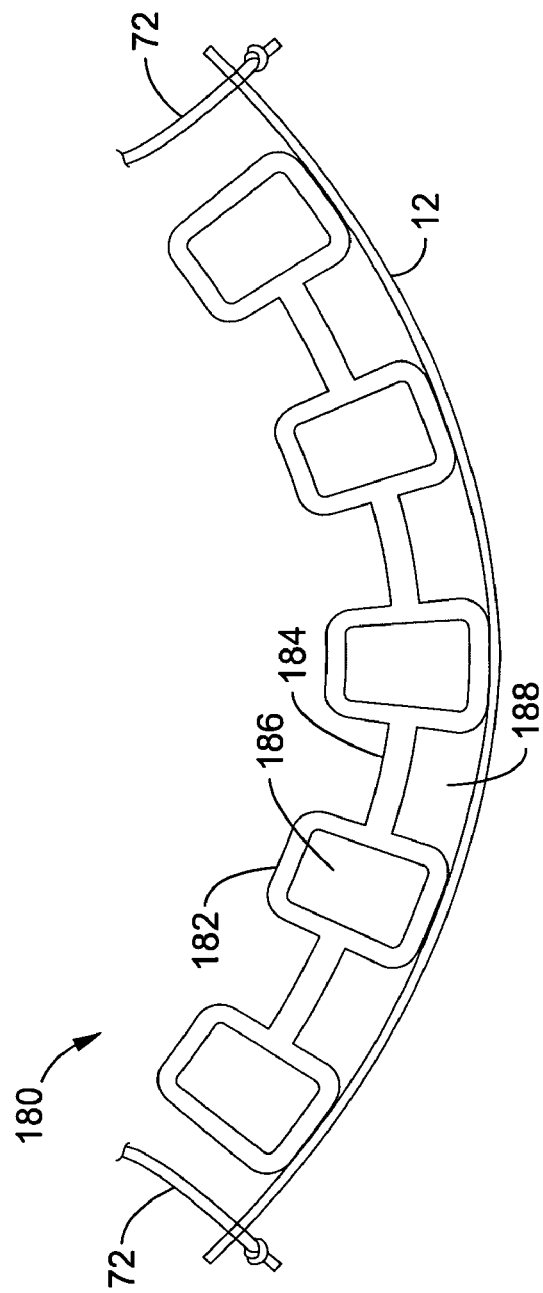

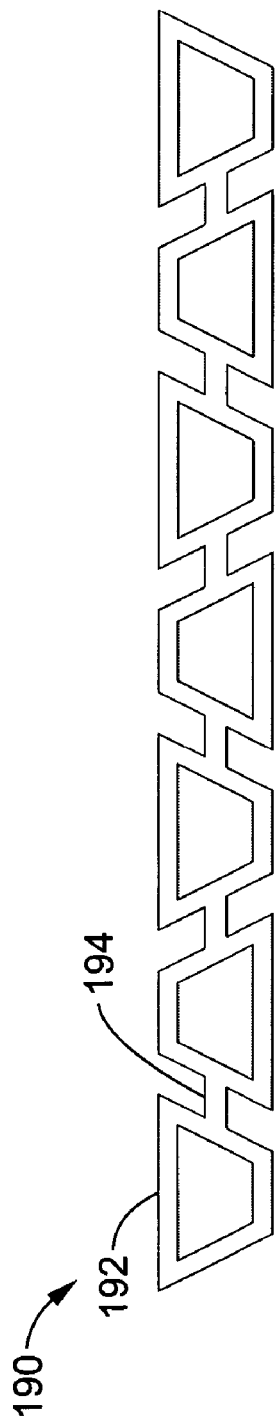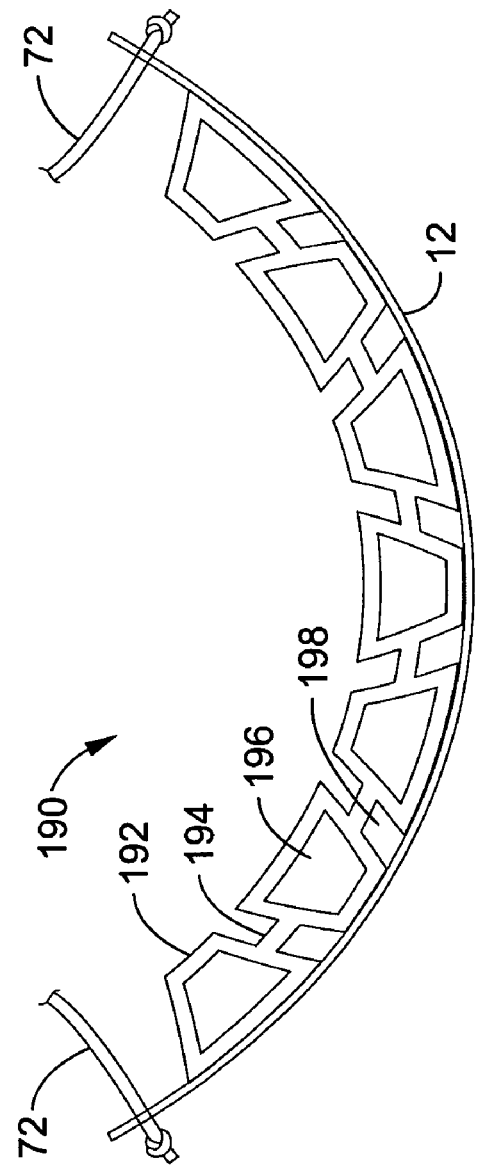
FIG. 22A
FIG. 22B

VENTILATED FACE SHIELD ASSEMBLY WITH GLARE SHIELD

CROSS-REFERENCE TO RELATED APPLICATIONS

This application claims priority from U.S. provisional application Ser. No. 60/560,801 filed on Apr. 7, 2004, incorporated herein by reference in its entirety, and from U.S. provisional application Ser. No. 60/578,625 filed on Jun. 9, 2004, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

The present invention pertains to head-mounted face shields and more particularly to a light weight, disposable, ventilated, face shield having an integrated glare shield.

2. Description of Related Art

In a number of industries, such as medical, dentistry, veterinary and laboratory, the use of a face shield provides protection for the eyes and face of the wearer from debris, splatters or pathogens. Increasingly, face shields are being utilized for preventing infections that can occur as a result of bodily fluid splattering that can arise within a number of occupations. A number of factors affect the acceptance of a face shield design, including comfort, ventilation, weight, ability to be securely retained in position, cost, and aesthetic considerations. The need for secure positioning and ventilation, which increases comfort while reducing the possibility of fogging, can be critical performance factors, especially in situations in which the face shield needs to be worn for extended periods of time.

Additionally, glare control is an important consideration for medical personnel working under bright lights, outdoors or who wear glasses under the face shield. Glare causes eye fatigue and facial fatigue from squinting and can contribute to loss of productivity or errors over an extended period of time. In certain light conditions, parts of eye glasses worn by the user are reflected on the inside of a face shield thereby interfering with vision through the face shield.

Medical face shields are used to prevent transfer of pathogens and, during use, can become contaminated by these pathogens. Therefore, disposable face shields are highly desired. To be practical, disposable face shields should be low cost and easy to use by the wearer. Since face shield assemblies are typically a three dimensional shape when worn, a kit that allows face shield components to be packaged and shipped in a compact, flat configuration and assembled at the point of use is desirable.

A number of examples of practical face shields exist. Examples of face shields which are being increasingly utilized in a number of industries may be found in U.S. Pat. No. 4,852,186; U.S. Pat. No. 4,864,653; U.S. Pat. No. 4,964,171; U.S. Pat. No. D375,583; U.S. Pat. No. 5,692,522; and U.S. Pat. No. 6,016,808; each of which is incorporated herein by reference. The above face shields provide numerous benefits. It will be appreciated, however, that the growing market for face shields is always in search of improved face shield designs that provide increasing utility, comfort, and style while reducing material requirements and manufacturing costs.

Therefore, a need exists for a lightweight, low-cost face shield with a glare shield that provides ample ventilation, and which can be manufactured at low cost and packaged compactly. The present invention satisfies those needs, as well as others, and overcomes the deficiencies of previously developed face shield designs.

BRIEF SUMMARY OF THE INVENTION

The present invention is a ventilated face shield assembly and method of forming a lightweight face shield with a glare shield that provides enhanced ventilation, glare control and comfort. The embodiments of face shields described herein are designed to be lightweight, easy to manufacture and adapted to be packaged and shipped in a flat configuration for later assembly at the point of use.

The ventilated face shield assembly generally comprises a flexible, transparent face shield, a flexible glare shield that projects over the face of the user, and a lightweight forehead spacer that positions the transparent face shield in separation from both the front and sides of the wearer's face while improving ventilation and reducing the opportunity for fogging of the face shield. The glare shield is configured to control glare and provide debris protection with ventilation and can be of a transparent, semi-transparent, translucent or opaque generally planar or sheet material. The glare shield or forehead spacer may be attached to the face shield when received by a user, or may be assembled at the time of use, depending on the need.

A means for retaining the face shield on the head of the wearer holds the face shield and glare shield in arcs on different planes. This configuration allows the face shield to generally maintain its three dimensional shape without the need for a stiffening member such as a frame or stiff visor. In a preferred embodiment, the means for retaining and means for fastening may be integrated into one element such as a cord with knotted ends or ends secured with a bead clamp. In another beneficial embodiment, the means for retaining can be integrated into a separate element such as a face or filter mask with retaining loops or straps. In a further embodiment, the means for spacing and the glare shield can be integrated into one element.

It is contemplated that typically the ventilated face shield assembly will be made available with a glare shield pre-attached, wherein the user need only connect the fasteners between the face shield and glare shield prior to use. Coupling the face shield and glare shield at the point of use can provide a significant reduction in storage volume. Furthermore the spacing means may be configured for compact storage and attached at the point of use to further reduce storage requirements. These user-assembled face shield assemblies could be considered "kits", wherein the user connects the elements of face shield, spacer, glare shield and retainer. It will be appreciated that one or more of these elements may be optional or preassembled.

In another embodiment, the spacing means is a forehead strap that holds the face shield in an arcuate configuration and provides ventilation between the forehead strap and face shield. In a still further embodiment, the spacing means is positioned at or near the inner edge of the glare shield.

The glare shield is preferably configured to shade the eyes and front and sides of the face in an arcuate configuration and in a position to protect the eyes and face from falling debris.

Fasteners known in the art such as hook and loop pads, contact adhesive, snaps, pins or interlocking tabs may be used to couple the mating ends of the glare shield and face shield.

An embodiment of the invention is a face shield having a planar configuration and an arcuate configuration, a glare shield coupled to the face shield, the glare shield having a planar configuration and an arcuate configuration, means for fastening adapted to couple the face shield in the arcuate configuration to the glare shield in the arcuate configuration, means for spacing coupled to the face shield, where the means for spacing is adapted to position the face shield to protect the face of the wearer when the face shield is in the arcuate configuration, where the glare shield in the arcuate configuration is adapted to control glare when fastened to the face shield by the fastening means, and where the face shield and the glare shield are adapted for flat storage when in their respective planar configurations.

Another aspect of the invention is where the means for spacing comprises the glare shield in the arcuate position when coupled to the face shield by the fastening means.

A further aspect of the invention is where the face shield material is selected from the group consisting of polystyrene, acrylic, acetate, polyethylene, terephthalate, and polycarbonate.

A still further aspect of the invention is where the glare shield material is selected from the group consisting of polystyrene, acrylic, acetate, polyethylene, terephthalate, and polycarbonate.

Another aspect of the invention is where the glare shield comprises a material through which light transmission is limited.

A further aspect of the invention is where the means for spacing comprises a flexible headband having ventilation apertures.

A still further aspect of the invention is where the means for fastening comprises a plurality of flexible hinges coupling the face shield to the glare shield, and a flexible cord having first, second ends, where the first, second ends are configured to couple the face shield in the arcuate configuration to the glare shield in the arcuate configuration when the cord is placed in a tension state.

Another aspect of the invention is means for retaining coupled to the face shield, where the retaining means is adapted to maintain the face shield in the arcuate configuration, and where the retaining means is further adapted to maintain the face shield in position to protect the face of the wearer.

A further aspect of the invention is a flexible cord having first, second ends, where the first, second ends are configured to couple the face shield in the arcuate configuration to the glare shield in the arcuate configuration when the cord is placed in a tension state, and where the means for spacing maintains the face shield in position to protect the face of the wearer when the cord is placed in a tension state.

A still further aspect of the invention is where the means for spacing comprises a flexible headband having ventilation apertures.

Another aspect of the invention is where the flexible headband has a compressed state adapted for flat storage.

A further aspect of the invention is where the means for spacing comprises a flexible headband having alternating slits, where the headband is expanded lengthwise prior to coupling to the face shield, and where expansion of the headband forms triangular ventilation spaces at the slits.

A still further aspect of the invention is where the means for spacing comprises a strip of flexible material having first and second ends, first and second apertures positioned at the first, second ends, the first and second apertures adapted to cooperate with the two ends of the cord, where the strip is adapted to position the face shield to protect the face of the wearer when tension is placed on the cord.

Another aspect of the invention is where the spacing means comprises the glare shield in the arcuate position when coupled to the face shield by the fastening means.

A further aspect of the invention is where the fastening means comprises a plurality of flexible hinges coupling the glare shield to the face shield.

A still further aspect of the invention is a cord keeper adapted to couple to the flexible cord at the first, second ends of the flexible cord, the cord keeper comprising first and second mating hollow hemispheres, the first hemisphere having a bridge, the bridge positioned across the diameter of the first hemisphere, the second hemisphere hingedly coupled to the first hemisphere, the second hemisphere having a pair of barbed ridges, the barbed ridges oriented parallel to the bridge, the barbed ridges protruding outside of the second hemisphere, the barbed ridges adapted to grasp the bridge when the first and second hemispheres are mated, where when the cord is positioned perpendicular on the bridge, and the second hemisphere is mated with the first hemisphere, the cord is secured between the bridge and the barbed ridges, and the first hemisphere is secured to the second hemisphere by the barbed ridges grasping the cord on the bridge.

Another aspect of the invention is a protective breathing mask coupled to the face shield, the protective breathing mask further comprising a pair of ear loops, where the face shield is maintained in an arcuate configuration when tension is place on the ear loops, and where the face shield is positioned to protect the face of the wearer when the ear loops are positioned on the ears of the wearer.

A further aspect of the invention is where the means for spacing comprises the glare shield in the arcuate configuration, and where the means for fastening comprises a plurality of hinges coupling the glare shield to the face shield.

A still further aspect of the invention is where the face shield and the glare shield are cut from a single sheet of material with the connection therebetween comprising a hinge.

Another embodiment of the invention is an apparatus for protecting the face of a wearer and controlling glare that comprises a face shield having a planar configuration and an arcuate configuration, a glare shield coupled to the face shield, the glare shield having a planar configuration and an arcuate configuration, a fastener adapted to couple the face shield in the arcuate configuration to the glare shield in the arcuate configuration, a spacer coupled to the face shield, where the spacer is adapted to position the face shield to protect the face of the wearer when the face shield is in the arcuate configuration, where the glare shield in the arcuate configuration is adapted to control glare when fastened to the face shield by the fastener, and where the face shield and the glare shield are adapted for flat storage when in their respective planar configurations.

Another aspect of the invention is providing a face shield assembly which is inexpensive to manufacture.

Another aspect of the invention is providing a face shield assembly with a glare shield adapted for assembly by end-users.

Another aspect of the invention is providing a well ventilated face shield assembly in which air can freely flow through the face shield spacer.

Another aspect of the invention is providing a face shield assembly upon which the transparent shield is retained away from the face of the wearer including the peripheral areas so as to encourage airflow and reduce fogging.

Another aspect of the invention is providing a face shield assembly that stores compactly and is assembled at the point of use.

Further aspects and advantages of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 2 is a cut-away side view of the ventilated face shield assembly as shown in FIG. 1.

FIG. 3 is profile view of the ventilated face shield assembly in FIG. 1 mounted on the head of a wearer.

FIG. 4 is a detail view of a hinge for a ventilated face shield as shown in FIG. 1.

FIG. 5 is a detail view of another embodiment of a hinge for a ventilated face shield shown in FIG. 1.

FIG. 6 is a detail view of a further embodiment of a hinge for a ventilated face shield shown in FIG. 1.

FIG. 9 illustrates a top view of the ventilated face shield assembly shown in FIG. 8 with the hinges attached to the face shield and tension put on the cord ends.

FIG. 19A illustrates a plan view of a rectangular piece of foam with a rectangular cut pattern that will form two ventilated headbands.

FIG. 19B illustrates a plan view of one headband separated from the cut pattern shown in FIG. 19A.

FIG. 19C illustrates a plan view of the headband shown previously in FIG. 19A and FIG. 19B affixed to the top inside surface of a face shield.

FIG. 20A illustrates a plan view of another embodiment of a ventilated headband with a cut pattern consisting of a profile of adjoining hollow circles and joined to a flat strip.

FIG. 20B illustrates a plan view of the ventilated headband in FIG. 20A affixed to the top inside surface of a face shield.

FIG. 20C illustrates a plan view of the headband shown in FIG. 20A compressed in a configuration for shipping or storage.

FIG. 21A illustrates a plan view of another embodiment of a ventilated headband with a cut pattern profile consisting of hollow rectangles with a thin joining strip in the center between the rectangles.

FIG. 21B shows a plan view of the headband in FIG. 21A affixed to the top inside surface of a face shield.

FIG. 22A illustrates a plan view of another embodiment of a ventilated headband with a cut pattern profile consisting of hollow alternating trapezoids with a thin joining strip in the center between the trapezoids.

FIG. 22B shows a plan view of the headband in FIG. 22A affixed to the top inside surface of a face shield.

DETAILED DESCRIPTION OF THE INVENTION

Referring more specifically to the drawings, for illustrative purposes the present invention is embodied in the apparatus generally shown in FIG. 1 through FIG. 28. It will be appreciated that the apparatus may vary as to configuration and as to details of the parts, and that the method may vary as to the specific steps and sequence, without departing from the basic concepts as disclosed herein.

In the context of this invention, inside surface refers the surface facing the wearer when a ventilated face shield is worn. Left and right are from a position facing the wearer when a ventilated face shield is worn.

Figure 1:
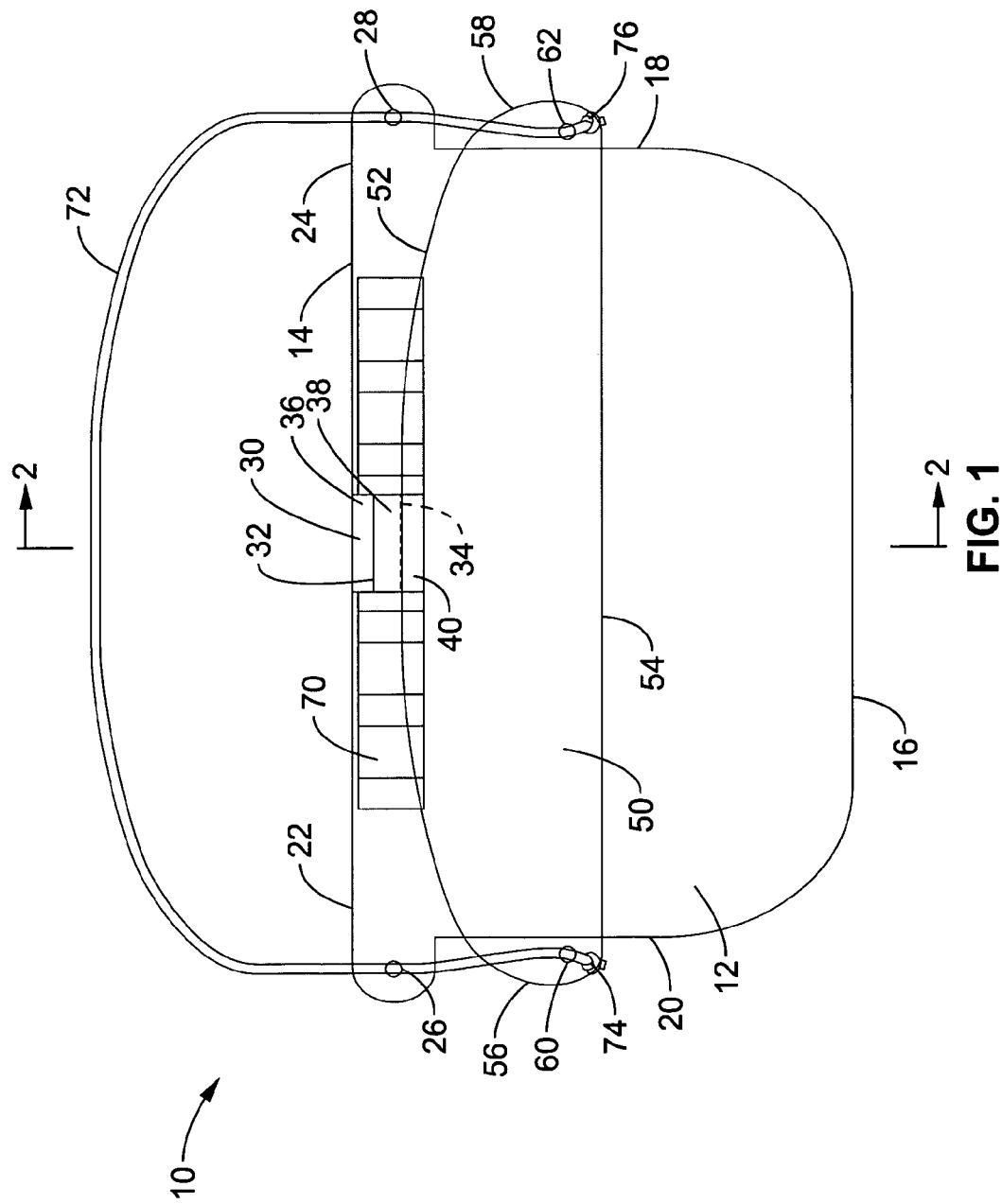
FIG. 1 is a plan view of a ventilated face shield assembly in a flat state and according to the invention.

FIG. 1 through FIG. 3 illustrate an embodiment of a ventilated face shield assembly, according to the present invention. In FIG. 1, a ventilated face shield assembly 10 is assembled and configured prior to use. A face shield of transparent flexible sheet material 12 is configured to cover the front and both sides of the face as well as the forehead and below the chin of a wearer. In other embodiments, face shield 12 is configured to cover primarily the eyes and is preferably used with a separate filter mask. Face shield 12 is cut generally rectangular with a top edge 14, bottom edge 16, right edge 18 and left edge 20. In this embodiment, the corners between bottom 16 and right, left edges 18, 20 are rounded. Left, right tabs 22, 24 extend out from the intersection of right, left edge 18, 20 and top edge 14. Left, right tabs 22, 24 each have a corresponding left, right apertures 26, 28. In a preferred embodiment, face shield 12 is made of sheet material consisting of polymeric materials. Suitable polymeric materials for face shield 12 include polystyrene, acrylic, polyethylene, acetate, terephthalate, and polycarbonate. Face shield 12 can be a uniform sheet or have pre-positioned creases to modify the arcuate position for better vision, comfort or ventilation. In one embodiment, face shield 12 is about 7½ inches long and about 12 inches wide with tabs extending sideways about 1 inch along the top edge 14 of face shield 12. Left, right apertures 26, 28 are spaced about 13 inches apart.

A hinge 30 is formed from a sheet of stiff but flexible material and has first, second creases 32, 34 to form three adjacent sections labeled 36, 38 and 40. In another embodiment, hinge 30 is formed from an injection molding process. In one embodiment, each crease 32, 34 of hinge 30 is bent to 90 degrees so the profile of the three sections 36, 38 and 40 form a flat "U" with crease 32, acting as a hinge between sections 36, 38 and crease 34 acting as a hinge between sections 38, 40 (see FIG. 2). The top outside edge of section 36 of hinge 30 is aligned with the top edge 14 of face shield 12. In the present embodiment, section 36 of hinge 30 is attached to the outside surface of face shield 12 at the center of top edge 14.

A flexible glare shield 50 is cut from a transparent, semi-transparent, translucent, tinted or opaque generally planar sheet material and is shaped generally as a crescent. In the present embodiment, glare shield 50 has an outer curved edge 52, an inner straight edge 54 and left right rounded ends 56, 58. In other embodiments, the inner edge 54 of glare shield 50 is slightly arcuate and/or outer edge 52 more arcuate. In a preferred embodiment, glare shield 50 is made of sheet material consisting of polymeric materials. Suitable polymeric materials for the glare shield include polystyrene, acrylic, polyethylene, acetate, terephthalate, and polycarbonate. In another embodiment, glare shield 50 is made from a stiff fabric, screen, perforated material or cellular foam material. In a further embodiment, glare shield 50 has ventilation apertures or is formed from a fabric or screen material with inherent ventilation properties. Optical properties can be imparted to glare shield 50 by tinting, spraying, curing, coating, laminating, etching, printing, screen overlay, or applying film to the glare shield with materials known in the art. In a preferred embodiment, glare shield 50 has optical properties similar to sunglasses. Face shield 12 can be similarly treated to provide desired optical properties. Glare shield 50 is preferably configured to shade the eyes and front and sides of the face.

Left, right apertures 60, 62 are positioned at each end of glare shield 50 and adapted to align with the left, right apertures 26, 28 in tabs 22, 24 of face shield 12 when face shield assembly 10 is positioned for wearing. In the present embodiment, the inside surface at the center of outer edge 52 of glare shield 50 is affixed to section 40 of hinge 30. In an alternative embodiment, the outside surface at the center of outer edge 52 of glare shield 50 is affixed to section 40 of hinge 30. In an exemplary embodiment, glare shield 50 is about 13 inches long and about 3 inches wide at the widest point in the crescent The spacing of apertures 60, 62 in glare shield 50 is approximately ½ inch less than the spacing of apertures 26, 28 in face shield 12 when both members are in a flat configuration.

A ventilated head band 70, constructed of cellular foam, rubber, plastic, sponge, corrugated paper, reinforced fabric or other flexible material provides a spacing means which is affixed to the inside surface of face shield 12 near top edge 14 and centered between left, right tabs 22, 24 and extends generally from about one-half to the full width of the face shield. Injection molded plastic may also be used alone or in combination with other materials to form head band 70. Preferably head band 70 functions as a means for spacing face shield 12 from the face of the wearer and preferably will provide a space of at least three quarters of an inch to about two to four inches of space in front of the wearer's face. A cushioning or absorbent material may also be incorporated with headband 70 for added comfort or to prevent sweat from dropping into the eyes of the wearer or the inside of face shield 12. In one embodiment (not shown), ventilated head band 70 extends over left, right tabs 22, 24. Head band 70 is configured to provide ventilation apertures (as will be shown in FIG. 18A through FIG. 22B) to allow air to flow past the face of the wearer and exit through the headband.

The means for retaining face shield assembly 10 on the face of a wearer may be implemented as a head harness, head band, cord or sturdy visor with the capability to secure face shield assembly 10 to the face of the wearer without undue force or tightness. In other embodiments, the means for retaining is attached to separate headgear, head harness, breathing masks, nose bridge supports or optical frames worn on the nose. In the embodiment illustrated here, a flexible cord 72 has first, second ends 74, 76 and which are threaded loosely from the inside surface of the face shield through apertures 26, 28 in left, right tabs 22, 24, then through apertures 60, 62 from the inside surface of the glare shield. In other embodiments, cord 72 can be elastic or a band, ribbon or strap. A knot is put in each end 74, 76 of cord 72 adjacent to the outside surface of glare shield as a means for fastening glare shield 50 to face shield 12. The body of cord 72 remains adjacent to the inside surface of face shield 12 and, in the present embodiment, cord 72 functions as the means for retaining and the means for fastening. In another embodiment, a cord keeper or other cord end securing means that will not pass through apertures 60, 62 can be attached to the ends 74, 76 of cord 72 as a means for fastening. Although fastening left, right ends 56, 58 of glare shield 50 to face shield 12 is preferred, fastening can be configured almost anywhere along the face shield 12 to glare shield 50 interface.

FIG. 2 illustrates a cut-away side view of the ventilated face shield assembly 10 shown in FIG. 1 and through line 2-2. Creases 32, 34 of hinge 30 are shown flexed for clarity but may be configured to lay flat during storage. Section 36 of hinge 30 is coupled to the outside surface of face shield 12 near top edge 14 and section 40 is coupled to the inside surface of glare shield 50 at top edge 52. In another embodiment (not shown), hinge 30 is coupled to the outside surface of glare shield 50. Headband 70 is affixed to the inside surface of face shield 12 near top edge 14.

FIG. 3 illustrates a profile view of the ventilated face shield assembly 10 shown in FIG. 1 and positioned to protect the face of a wearer 80, shown in phantom. Tension is put on cord 72 by looping around the back of the head of wearer 80 and the knots in the ends 74, 76 of cord 72 pull left, right glare shield apertures 60, 62 and left, right face shield apertures 26, 28 together. Glare shield 50 bows out farther than face shield 12. This causes glare shield 50 to orient in a different plane than the face shield 12 and causes the bottom edge 54 of glare shield 50 to tilt back over the head of the wearer 80 and in a position to control or eliminate glare on face shield 12 and the eyes of the wearer. Hinge 30 bends inward so that the top of section 36 and the bottom of section 40 are close or touching. Headband 70 contacts the forehead of the wearer 80 and assumes the arcuate shape of the forehead. Tension on cord 72 allows face shield 12 and glare shield 50 to maintain their three dimensional shape without the need for a stiffening member such as a frame or visor.

Headband 70 acts as a spacer to hold face shield 12 away from the nose and face of the wearer 80. Spaces in the headband (see FIG. 18A through FIG. 22B) provide ventilation inside face shield 12 while glare shield 50 extends over headband 70 to protect from falling debris. In a preferred embodiment, the space between the face of wearer-80 and face shield 12 accommodates optical eyewear. In further embodiments (not shown), optical accessories such as optical magnification systems, cameras or lights sources are coupled to face shield 12 and/or glare shield 50. Additional head straps or harnesses (not shown) can be used to support face shield assembly 10 or accessories. Further, face shield assembly 10 can be configured to fit over military helmets or other protective head gear.

FIG. 4 through FIG. 6 illustrate further embodiments of hinges used as fastening means for a ventilated face shield assembly according to the present invention.

FIG. 4 is a schematic illustration of three sided hinge 30 shown in FIG. 1 through FIG. 3 in a flat configuration with the stipple pattern designating contact adhesive on sections 36 and 40. The adhesive can be covered by non-stick plastic, paper or other peel away material so that hinge 30 can be applied to face shield 12 and glare shield 50 (shown in FIG. 1 through FIG. 3) just prior to use. In other embodiments (not shown), hinge 30 has four or more creases to optimally change the spacing and orientation between face shield 12 and glare shield 50. Hinge 30 with creases 32, 34 can also be formed by injection molding. In further embodiments (not shown), sections 36, 40 have increase thicknesses, such as by attaching foam rubber, to change spacing and orientation of the hinge in the folded position.

FIG. 5 is a schematic illustration of a flexible hinge 82 in a dumbbell pattern made from flexible sheet material with the stipple pattern designating contact adhesive as discussed in FIG. 4.

FIG. 6 illustrates another embodiment of a flexible hinge 84 with a dumbbell pattern shown in FIG. 5, but with the center circles representing a snap, hook and loop fabric pad or a rivet.

Figure 7:
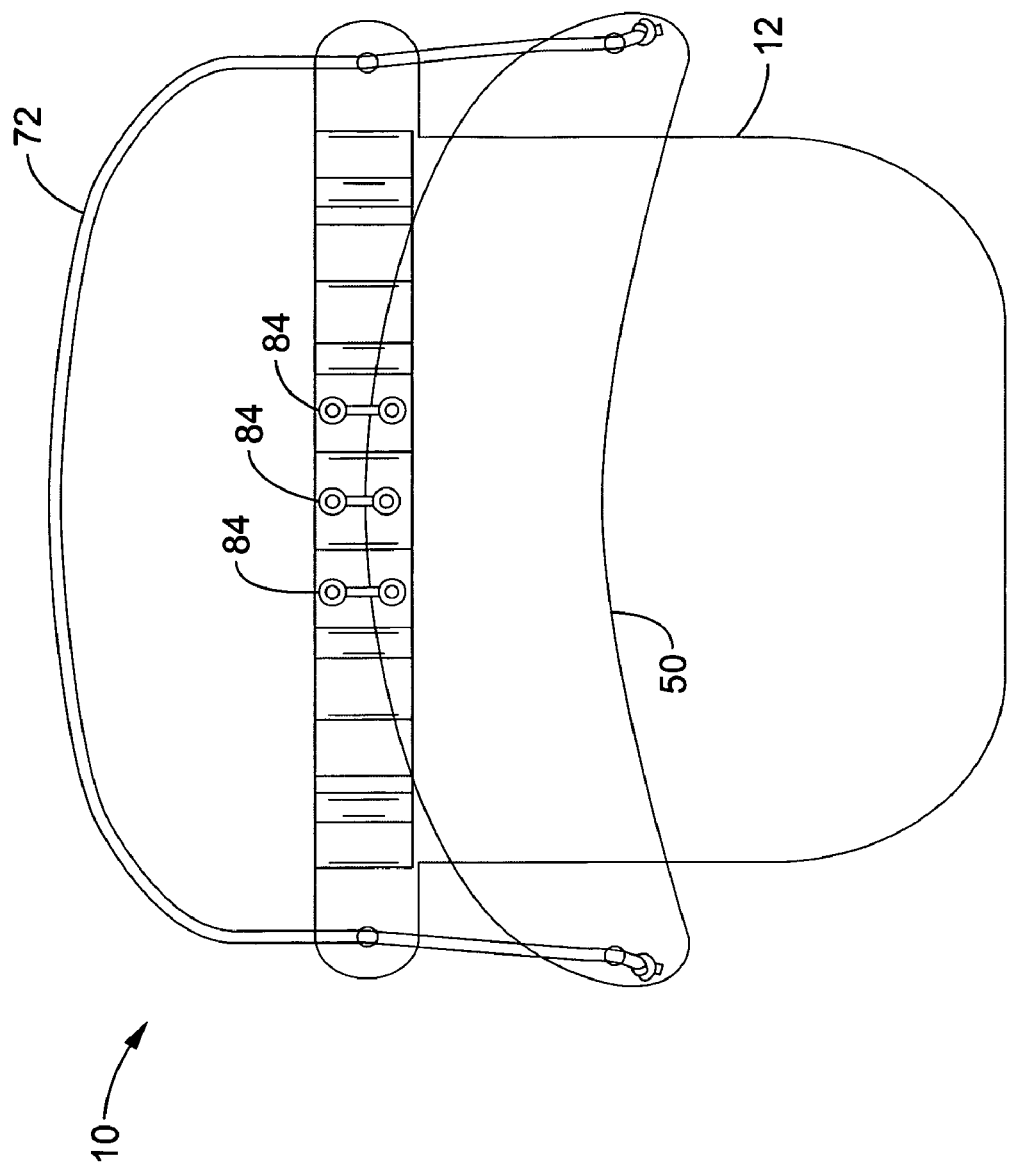
FIG. 7 is a plan view of a ventilated face shield assembly shown in FIG. 1, configured with hinges as shown in FIG. 6 coupling the face shield to the glare shield.

FIG. 7 illustrates an embodiment of a ventilated face shield assembly 10 similar to the one shown in FIG. 1, but with a plurality of flexible hinges 84 as shown in FIG. 6 coupling face shield 12 to glare shield 50.

Figure 8:
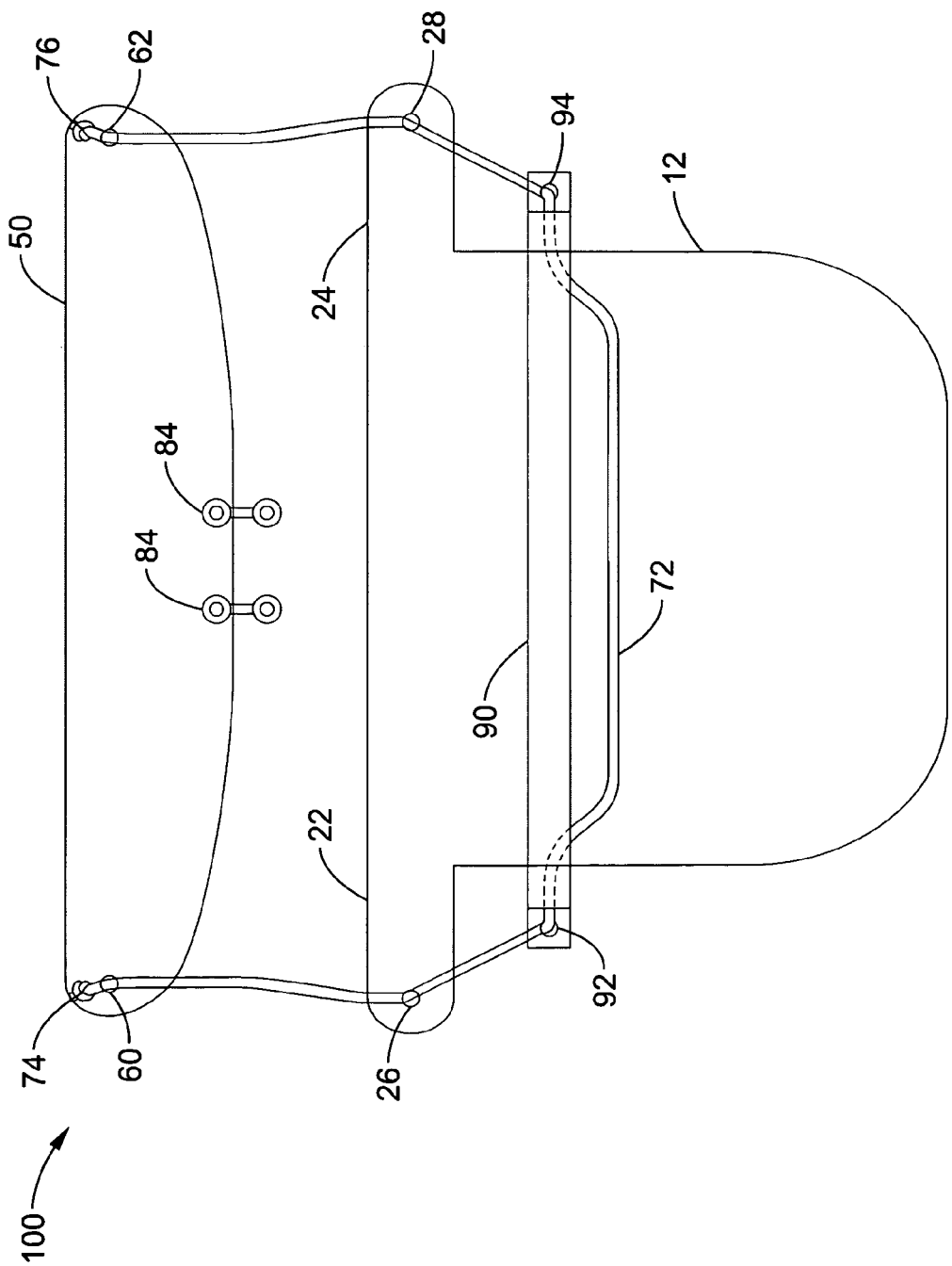
FIG. 8 illustrates a plan view another embodiment of a ventilated face shield assembly where the hinges have not yet been attached to the face shield and the ventilated headband is replaced with a forehead strap.

FIG. 8 and FIG. 9 illustrate another embodiment of a ventilated face shield assembly 100 where the ventilated headband is replaced with a forehead strap 90 as the spacing means. The forehead strap 90 is a strip of flexible thin material, preferably of the same material as face shield 12 and/or glare shield 50 to reduce manufacturing cost. Forehead strap 90 is preferably cushioned with absorbent material and has apertures 92, 94 at each end that are spaced closer than the apertures 26, 28 in the face shield tabs 22, 24 and the apertures 60, 62 in glare shield 50. Ends 74, 76 of cord 72 are threaded through the apertures 92, 94 in forehead strap 90, then through apertures 26, 28 in face shield 12 then through apertures 60, 62 in glare shield 50 and knotted in a manner shown in FIG. 1. Two flexible hinges 84, (as shown in FIG. 6), are coupled to glare shield 50 but not to face shield 12. In this configuration, the ventilated face shield assembly 100 can be stored and shipped in a flat compact configuration and assembled in the field by attaching flexible hinges 84 to face shield 12.

FIG. 9. illustrates a top view of the ventilated face shield assembly 100 shown in FIG. 8 with tension on cord 72. The flexible hinges 84 are coupled to face shield 12 in a manner similar to that shown in FIG. 7. The apertures 92, 94 in the forehead strap 90 are aligned with the apertures 26, 28 in face shield 12 and apertures 60, 62 in glare shield 50, by pulling cord 72 against the knots in ends 74, 76. The shorter forehead strap 90 holds the face shield 12 and the glare shield 50 in an arcuate configuration in a manner similar to that shown in FIG. 3. In use, forehead strap 90 is placed against the forehead and the cord is positioned around the back of the head of the wearer. The shorter length of the forehead strap 90 causes the face shield 12 to bow outward to provide a ventilated area between the forehead strap 90 and the face shield 12. Glare shield 50 folds over face shield 12 in a manner similar to that shown in FIG. 3 and provides glare protection and protection from objects falling into the ventilated space behind face shield 12.

FIG. 10 through FIG. 15 illustrate alternate embodiments for fastening the ends of glare shield 50 to the tabs of face shield 12 in a manner similar to that shown in FIG. 3.

Figure 10:
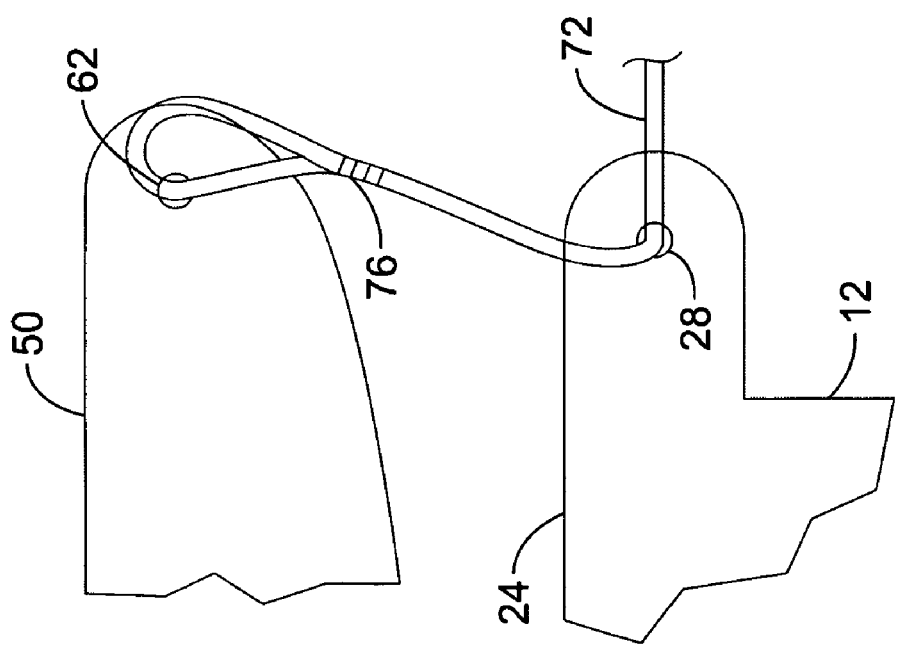
FIG. 10 illustrates a plan view of threading the cord through the glare shield and the tabs of the face shield of a ventilated face shield assembly as shown previously in FIG. 1, and fusing the end of the cord to itself.

FIG. 10 illustrates the end 76 of cord 72 threaded through aperture 28 of face shield 12 and aperture 62 of glare shield 50 then looped around and fused, such as by welding, to cord 72.

Figure 11:
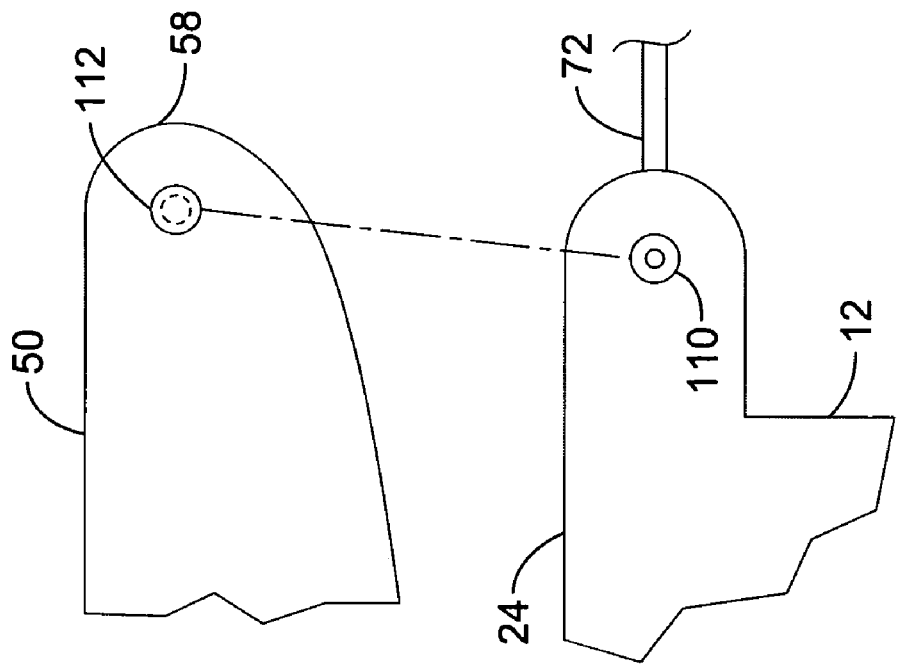
FIG. 11 illustrates a plan view of coupling the ends of the glare shield to the tabs of the face shield of a ventilated face shield assembly as shown previously in FIG. 1 with a snap.

In FIG. 11, a male snap 110 on tab 24 of face shield 12 is mated with a female snap 112 on the end 58 of the glare shield. Cord 72 is attached to tab 24 in a conventional manner.

Figure 12:
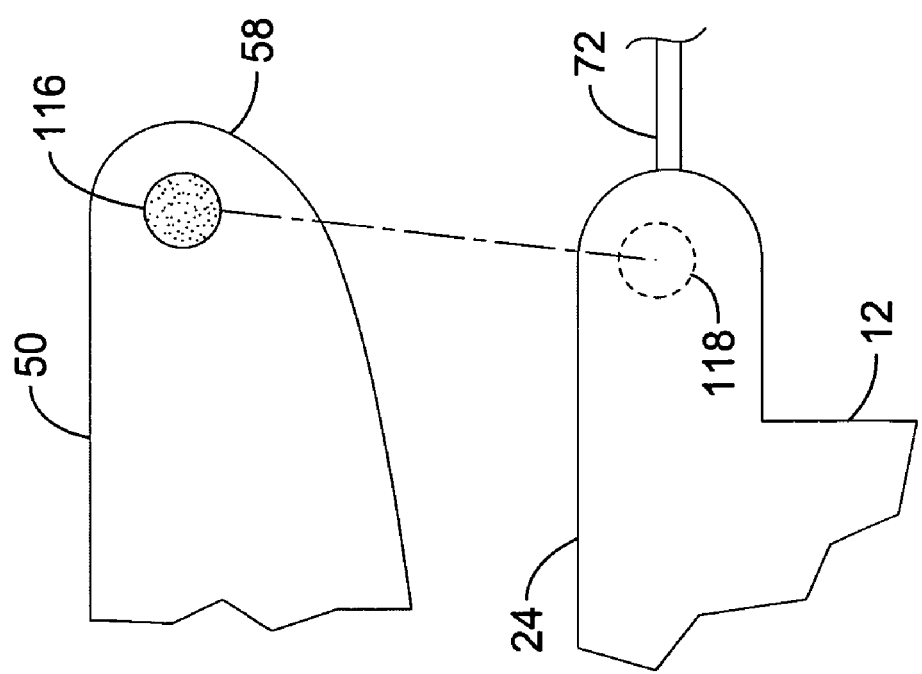
FIG. 12 illustrates a plan view an embodiment of coupling the ends of the glare shield to the tabs of the face shield of a ventilated face shield assembly as shown previously in FIG. 1 with contact adhesive or hook and loop fabric.

FIG. 12 illustrates schematically a contact adhesive, designated by a stipple pattern 116, on the end 58 of the glare shield 50 adapted to affix to a position 118 on tab 24 of face shield 12, designated by a dotted circle 118. Cord 72 is attached to tab 24 in a conventional manner. FIG. 12 also illustrates schematically another embodiment of the invention where, by substitution, a hook material is designated by stipple pattern 116 and a mating loop material is designated by dotted circle 118.

Figure 13:
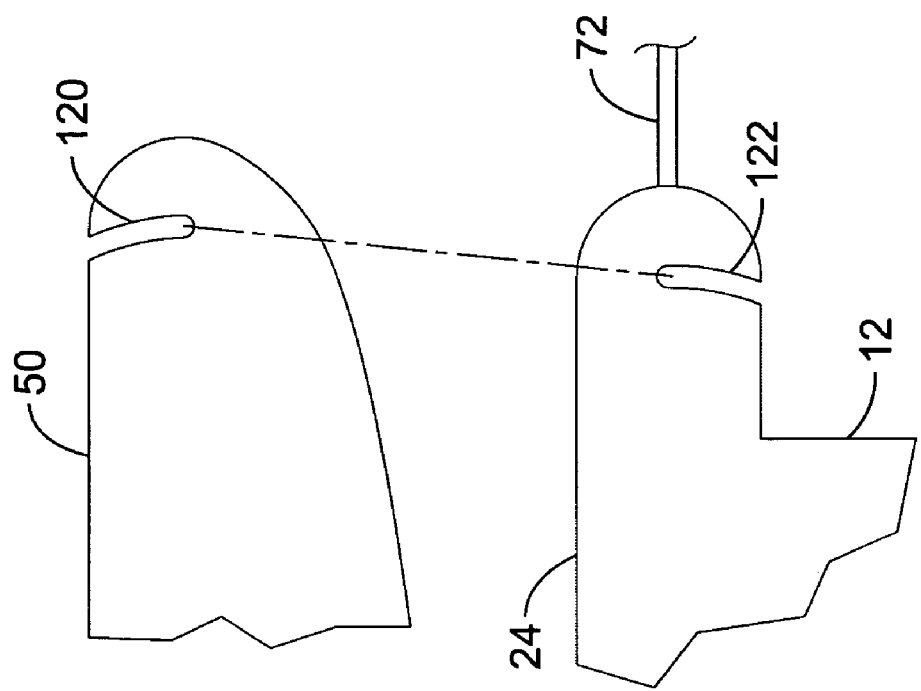
FIG. 13 illustrates a plan view of coupling the ends of the glare shield to the tabs of the face shield of a ventilated face shield assembly as shown previously in FIG. 1 with opposing mating slots.

FIG. 13 illustrates schematically an open end slot 120 in the end of the glare shield 50 and oriented generally upward, adapted to mate with an open end slot 122 in tab 24 of face shield 12 and oriented generally downward. The end of cord 72 is attached to tab 24 in a conventional manner.

Figure 14:
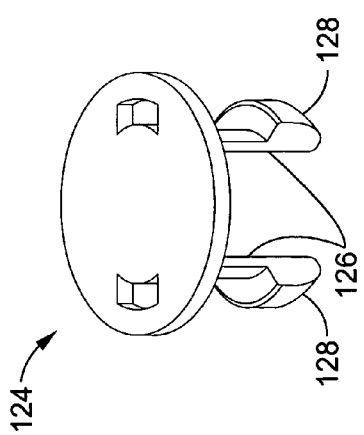
FIG. 14 illustrates a perspective view of a pop connector configured to mate aligned apertures of a glare shield and a face shield in a ventilated face shield assembly as shown previously in FIG. 1.

FIG. 14 illustrates a pop connector 124 configured to mate aligned apertures in a ventilated face shield assembly as shown previously in FIG. 1. Pop connector 124 is a disc with a diameter larger than the diameter of the aforementioned apertures. Two sets of flexible barb stems 126 with the nose 128 of the barbs pointing outward are coupled to the disc in a perpendicular orientation The barb stem 126 are oriented generally along a circle to mate with the circumference of the aforementioned apertures. The nose 128 of the barbs 126 are oriented to extend outward in a circle larger than the circumference of the apertures. In use, apertures 26, 28 of glare shield 50 and apertures 26, 28 of face shield 12 (shown in FIG. 1) are aligned and the nose 128 of barbs 126 are pushed through the aligned apertures until they penetrate past all aligned apertures. The outward facing noses 128 prevent the pop connector 124 from exiting the apertures without first exerting inward force against the barb stems 126. As described in FIG. 11 through FIG. 13, the end of the cord may attached to tabs 22, 24 (not shown) in a conventional manner. In a further embodiment, pop connector 124 is used to couple a hinge to a glare shield and/or a face shield.

Figure 16:
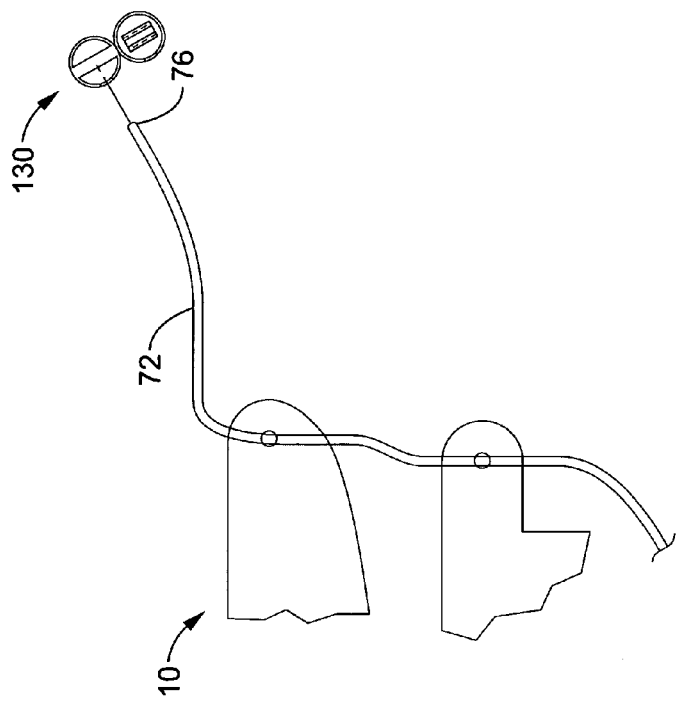
FIG. 16 illustrates a plan view of the cord keeper in FIG. 15 aligned with an end of a cord used on a ventilated face shield assembly as shown in FIG. 1.
Figure 15:
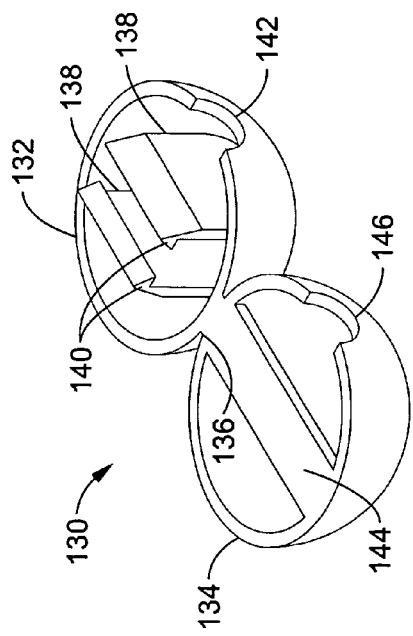
FIG. 15 illustrates a perspective view of an open cord keeper configured to secure the end of a cord according to the present invention.
Figure 17:
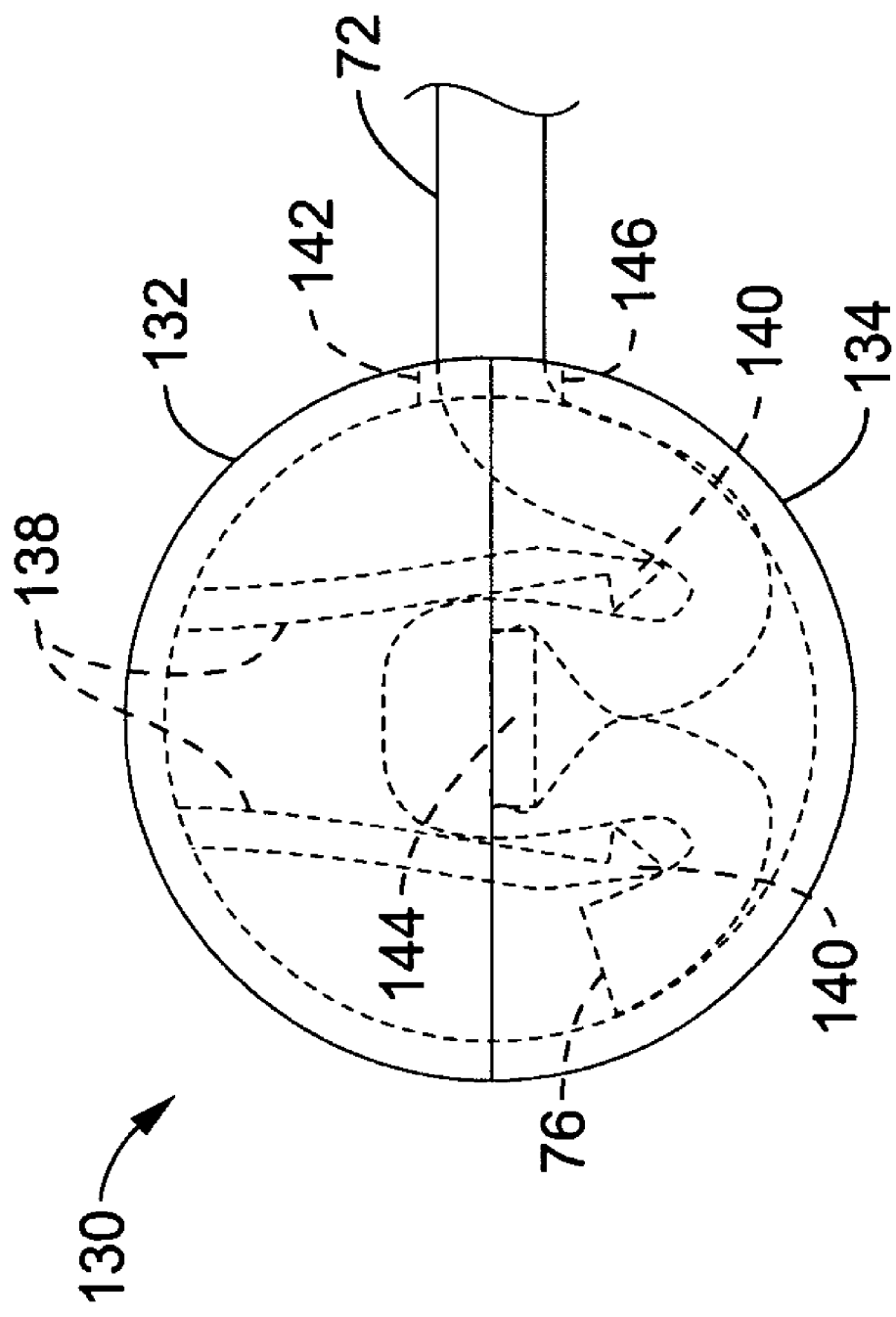
FIG. 17 is a cross section view of the cord keeper in FIG. 15 and FIG. 16 closed on the end of a cord.

FIG. 15 through FIG. 17 illustrate a cord keeper as a component for securing the end of the cord in a ventilated face shield assembly and according to the present invention.

FIG. 15 illustrates a perspective view of a cord keeper 130 as a first and second hollow hemispherical components 132, 134 coupled by a hinge 136 where the hinge is a section of flexible material or the same material as the hemispheres 132, 134. In one embodiment, cord keeper 130 is formed by injection molded plastic. First hemisphere 132 has two protruding, parallel, flexible ridges 138 oriented generally in line with the hinge. The protruding ridges 138 extend beyond the edge of hemisphere 132. the tops of the two ridges are configured as triangular barbs 140 with the barbs facing each other. A semicircle opening 142 for a cord is positioned on one side of the hemisphere edge and perpendicular to the ridges 138. Second hemisphere 134 has a bridge 144 spanning the opening of the hemisphere parallel to the ridges 138 with each end of bridge 144 fusing with the edge of second hemisphere 134. Bridge 144 is aligned with the ridges 138 and positioned so that the barbs 140 on the ridges 138 will securely grasp the bridge 144 when the two hemispheres 132, 134 are mated in a closed position. A semicircular opening 146 for a cord is positioned on one side of the edge of second hemisphere 134 and adapted to mate with the cord opening 142 in first hemisphere 132.

FIG. 16 illustrates the cord keeper in FIG. 15 aligned with an end of cord 72 used on a ventilated face shield assembly 10 as shown in FIG. 1. cord 72 is aligned with the cord openings 142, 146 and the end of the cord 76 is placed perpendicular across the bridge 144.

FIG. 17 is a cross section view of the cord keeper 130 in FIG. 15 and FIG. 16 closed over the end 76 of cord 72. Ridges 138 in first hemisphere 132 press the cord 72 down on both sides of the bridge 144 in second hemisphere 134 causing cord 72 to deform in a serpentine pattern over the bridge 144. Ridges 138 further exert compressive force on the cord 72 between the bridge 144 and the ridges 138. Barbs 140 on ridges 138 are adapted to grasp around the bridge 144 and hold cord keeper 130 closed while securing the end 76 of the cord 72 in the cord keeper 130.

FIG. 18A through FIG. 22B illustrate further embodiments of headbands for a ventilated face shield assembly 10 as shown previously in FIG. 1 through FIG. 3.

Figure 18C:
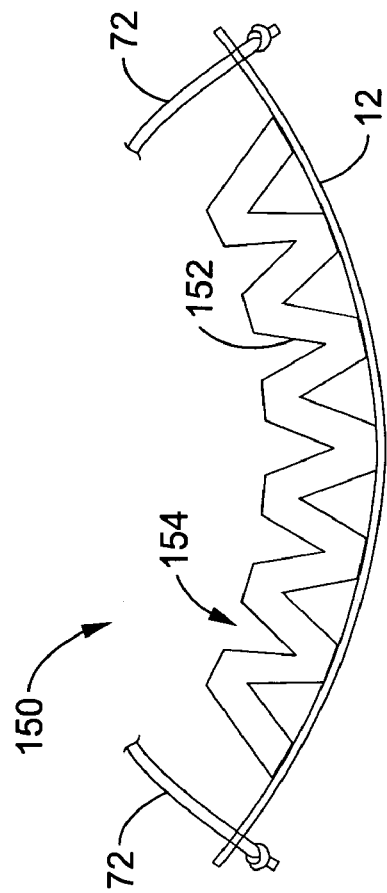
FIG. 18C illustrates a plan view of the headband shown previously in FIG. 18A and FIG. 18B affixed to the top inside surface of a face shield.
Figure 18A:
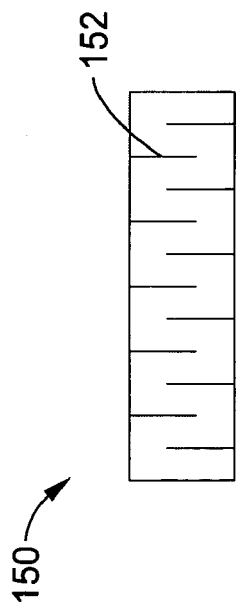
FIG. 18A illustrates a plan view of a rectangular piece of foam with a cut pattern that will form a ventilated headband according to the present invention.

FIG. 18A illustrates a rectangular piece of memory material such as foam 150 with a cut pattern 152 that will form a ventilated headband. In one embodiment, the foam piece 150 is preferably made of an inexpensive, soft, compressible material with a memory shape such as open cell foam. Other materials such as closed cell foam, expanded foam, sponge, plastic, rubber reinforced fabric or corrugated or folded paper materials are contemplated. In one preferred embodiment, foam piece 150 is about 6 inches long, 1 inch wide and about 1-2 inches thick in an uncompressed state. The alternating slits 152 cut in foam 150 are approximately ½ inch apart and end about ½ inch from the edge of the foam.

Figure 18B:
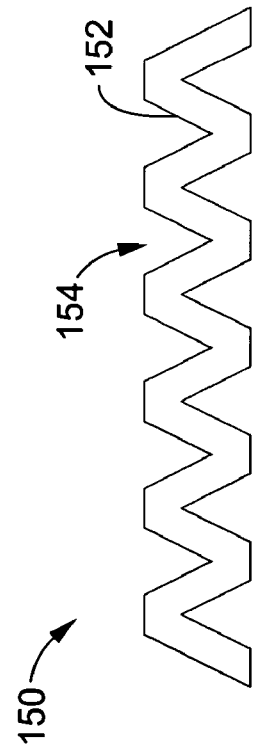
FIG. 18B illustrates a plan view of the cut foam in FIG. 18A expanded to form a continuous headband with triangular ventilated spaces.

FIG. 18B illustrates the cut foam piece 150 in FIG. 18A expanded to form a continuous headband with triangular ventilation spaces 154.

FIG. 18C illustrates the cut foam piece 150 shown previously in FIG. 18A and FIG. 18B affixed to the top inside surface of a face shield 12 forming a headband. Headband 150 can be affixed with a contact adhesive or other known adhesion methods. The headband 150 can be affixed to the face plate at the time of manufacturing or at the time of use. The pattern of the expanded headband 150 adapts to face shield 12 in an arcuate configuration and adapts to different forehead dimensions minimal or no compression of the foam. The present headband pattern offers minimal resistance to the arcuate position reducing tension required on the cord 72. Headband 150 provides spacing clearance for the face shield against the face and alternating ventilation openings 154 formed from slits 152 for the face and forehead. Note that the spacing clearance can be adjusted by adjusting the expansion of head band 150 before attaching to face shield 12.

FIG. 19A illustrates a rectangular piece of foam 160 with another cut pattern that will form a ventilated headband. This cut pattern 162 will provide two identical headbands 164, 166 from one piece of foam 160 and provides advantages in reducing storage volume or steps in production. The foam can be cut and shipped or stored in this configuration and separated into two headbands at the time of use.

FIG. 19B illustrates headband 166 separated from the cut pattern 162 shown in FIG. 19A. The cut pattern 162 forms ventilation openings 168 in headband 166.

FIG. 19C illustrates the headband 166 shown previously in FIG. 19A and FIG. 19B affixed to the top inside surface of a face shield 12. The headband 166 can be affixed with a contact adhesive or other known adhesion methods. This embodiment of headband 166 does not need to be expanded before affixing to the face shield 12 and adapts to different forehead dimensions with minimal or no compression of the foam. This headband pattern offers minimal resistance to the arcuate position of the face shield 12 reducing tension required on the cord 72. The headband provides clearance for face shield 12 against the face of the wearer and ventilation openings 168 for the face and forehead.

FIG. 20A illustrates another embodiment of a ventilated headband 170 made from a compressible memory material such as foam with a cut pattern consisting of a profile of hollow circles 172 joined together and joined to a flat strip 174. This cut pattern provides circular ventilation openings 176 and triangular ventilation openings 178 and provides a preferred ratio of space to material for beneficial weight and material use.

FIG. 20B illustrates the ventilated headband 170 in FIG. 20A affixed to the top of a face shield 12. Strip 174 of headband 170 can be affixed with a contact adhesive (i.e. covered with peel off tape) or other known adhesion methods. The pattern of headband 170 adapts to face shield 12 in an arcuate configuration and adapts to different forehead dimensions with minimal or no compression of the foam. This headband pattern offers minimal resistance to the arcuate position of the face shield reducing tension required on cord 72. Headband 170 provides clearance for the face shield 12 against the face and ventilation openings 176, 178 for the face and forehead.

FIG. 20C illustrates the headband 170 shown in FIG. 20A and FIG. 20B where ventilation openings 176, 178 are compressed flat in a configuration for shipping or storage but restore their memory shape for proper spacing when unpacked and coupled to the face shield. The pattern and the ratio of space to foam provides a preferred compressed configuration to reduce bulk for shipping and storage.

FIG. 21A illustrates another embodiment of a ventilated headband 180 made from a compressible memory material with a cut pattern profile consisting of hollow rectangles 182 with a thin joining strip 184 in the center between the rectangles. This cut pattern provides a preferred ratio of space to material for weight and material use and increased ventilation. This pattern can be compressed in a manner similar to the headband shown in FIG. 20C.

FIG. 21B shows the headband 180 in FIG. 21A affixed to the top of a face shield 12. The headband provides clearance for the face shield against the face and ventilation openings 186 in hollow rectangles 182 and ventilation spaces 188 adjacent joining strips 184 for the face and forehead. This embodiment also provides a beneficial reduced contact area, shown as spaces 188, between the headband 180 and face shield 12. Headband 180 can be compressed flat for storage in a manner shown in FIG. 20C.

FIG. 22A illustrates another embodiment of a ventilated headband 190 made from a compressible memory material such as foam with a cut pattern profile consisting of hollow trapezoids 192 with a thin joining strip 194 in the center between trapezoids 192. This cut pattern provides a preferred ratio of space to foam for weight and material use. This pattern can be compressed in a manner similar to the headband shown in FIG. 20C.

FIG. 22B shows the headband 190 in FIG. 22A affixed to the top of a face shield 12. Headband 190 provides clearance for the face shield against the face and ventilation openings 196 inside the trapezoids and ventilation openings 198 adjacent joining strips 194 for the face and forehead. This embodiment of a headband 190 provides a beneficial increased contact area to face shield 12 and to the forehead of the wearer on trapezoids 192, such as to absorb sweat.

In further embodiments, (not shown), individual balls, solid cylinders, hollow cylinders or hollow rectangles of memory material such as foam are affixed to face shield 12 in a regular spaced pattern along the top edge to form a headband. These foam components can be attached at the time of manufacture or at the time of use.

Figure 23:
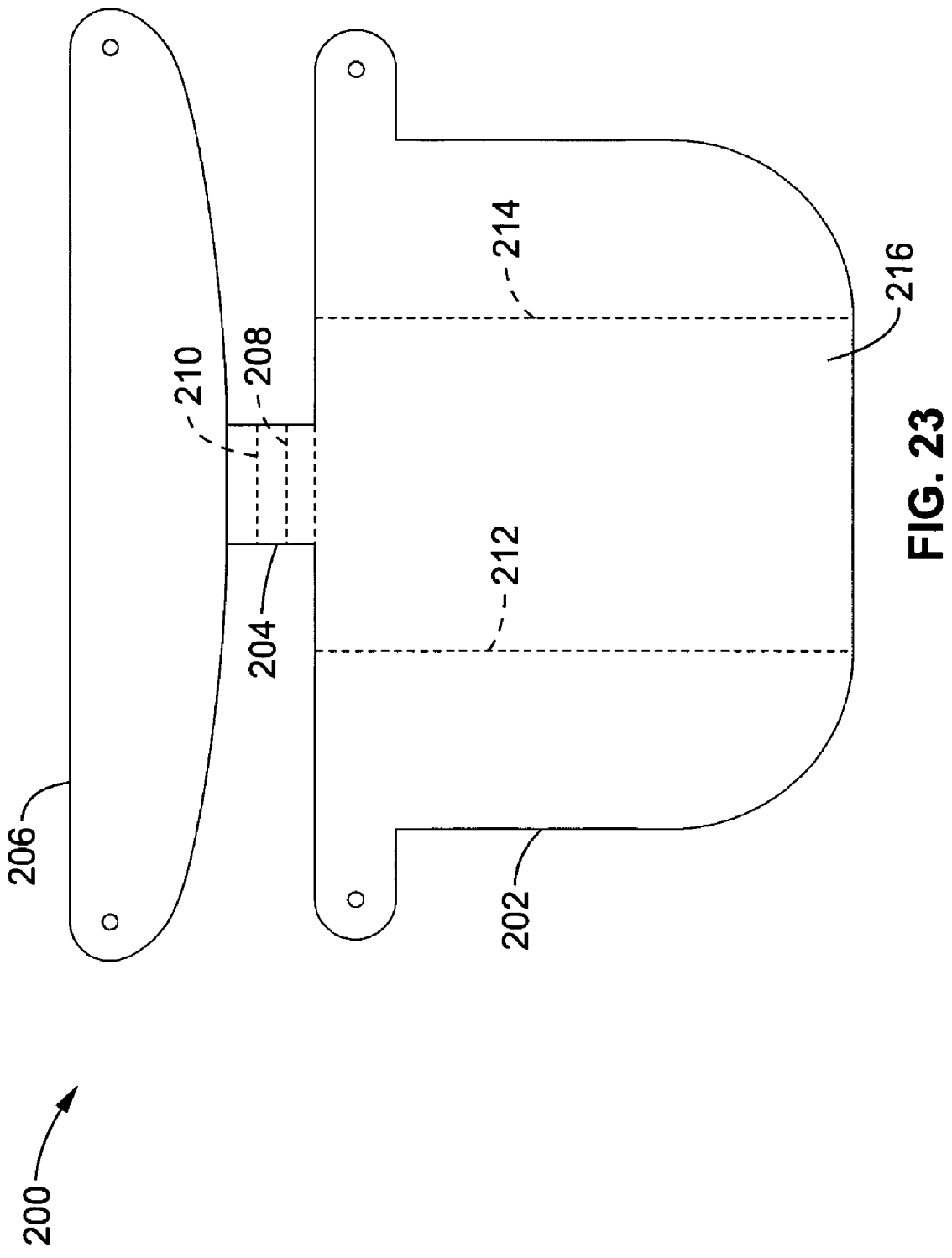
FIG. 23 illustrates a plan view of another embodiment of a ventilated face shield assembly where the face shield, hinge and glare shield are cut as a single piece from a sheet of material.

FIG. 23 illustrates another embodiment of a ventilated face shield assembly 200. Face shield 202, hinge 204 and glare shield 206 are cut as a single piece from a sheet of material. This embodiment has the advantage of planar storage of the components until assembled or used. Also the primary components cannot become separated in transport or storage. The sheet material can be transparent or have desired optical properties. The connecting material between the face shield portion and the glare shield portion comprises the hinge 204. Two crease lines 208, 210 in the hinge 204 form a hinge, similar to the three side hinge shown in FIG. 1 through FIG. 3. Optional vertical crease lines 212, 214 in face shield 202 are shown as a further embodiment where section 216 of face shield 202 forms a relatively flat viewing surface when face shield 202 is positioned in an arcuate position.

Figure 25:
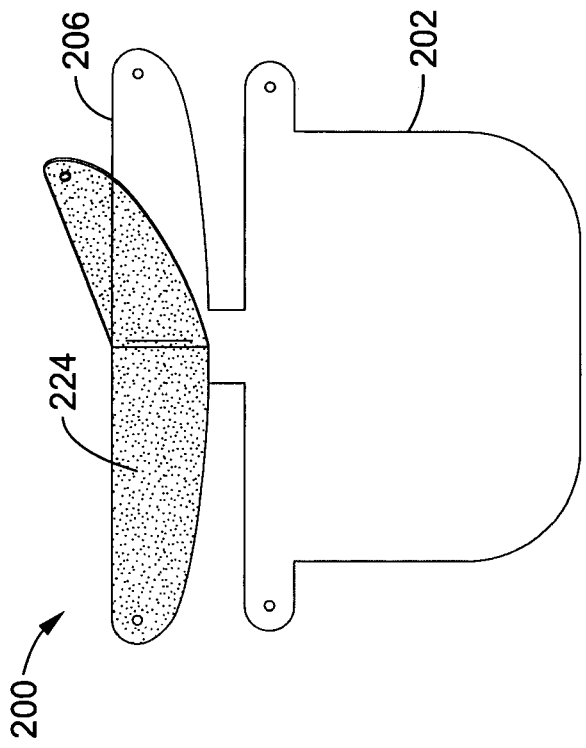
FIG. 25 is a schematic illustration of applying a tinted film or glare reducing film, designated by the stipple pattern, to the glare shield portion of the face shield assembly shown in FIG. 23.
Figure 24:
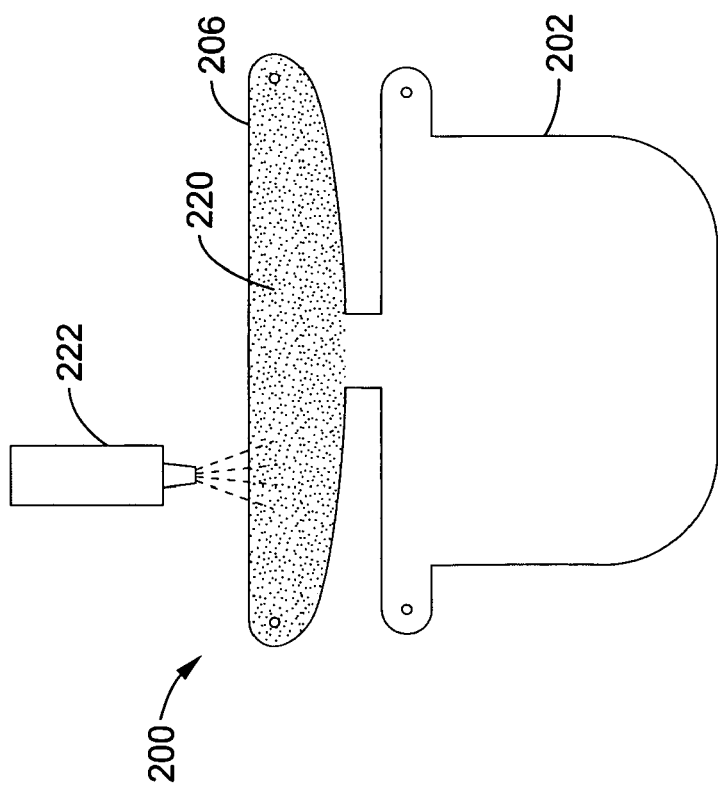
FIG. 24 is a schematic illustration of applying a tint or other glare treatment, designated by the stipple pattern, to the glare shield portion of the face shield assembly shown in FIG. 23 by spray, sputter or other coating methods.

FIG. 24 and FIG. 25 are schematic illustrations of applying a tint or other glare treatment to the glare shield portion of the face shield assembly 200 shown in FIG. 23.

In FIG. 24, the stipple pattern designates a preferred tint or glare control coating 220 being applied to the glare shield 206 of face shield assembly 200 by spray, sputter electrodeposition or other coating methods 222 known in the art. A glare or optical coating can also be applied to glare shield 206 by curing or etching methods (not shown) known in the art.

FIG. 25 illustrates a tinted film or glare reducing film, designated by the stipple pattern 224, being applied to glare shield 206 of face shield assembly 200. Optical properties can be imparted to the glare shield portion by tinting, laminating, printing, or applying one or more film layers 224. Perforations (not shown) may be added to impart optical or ventilation properties to glare shield 206.

Figure 26:
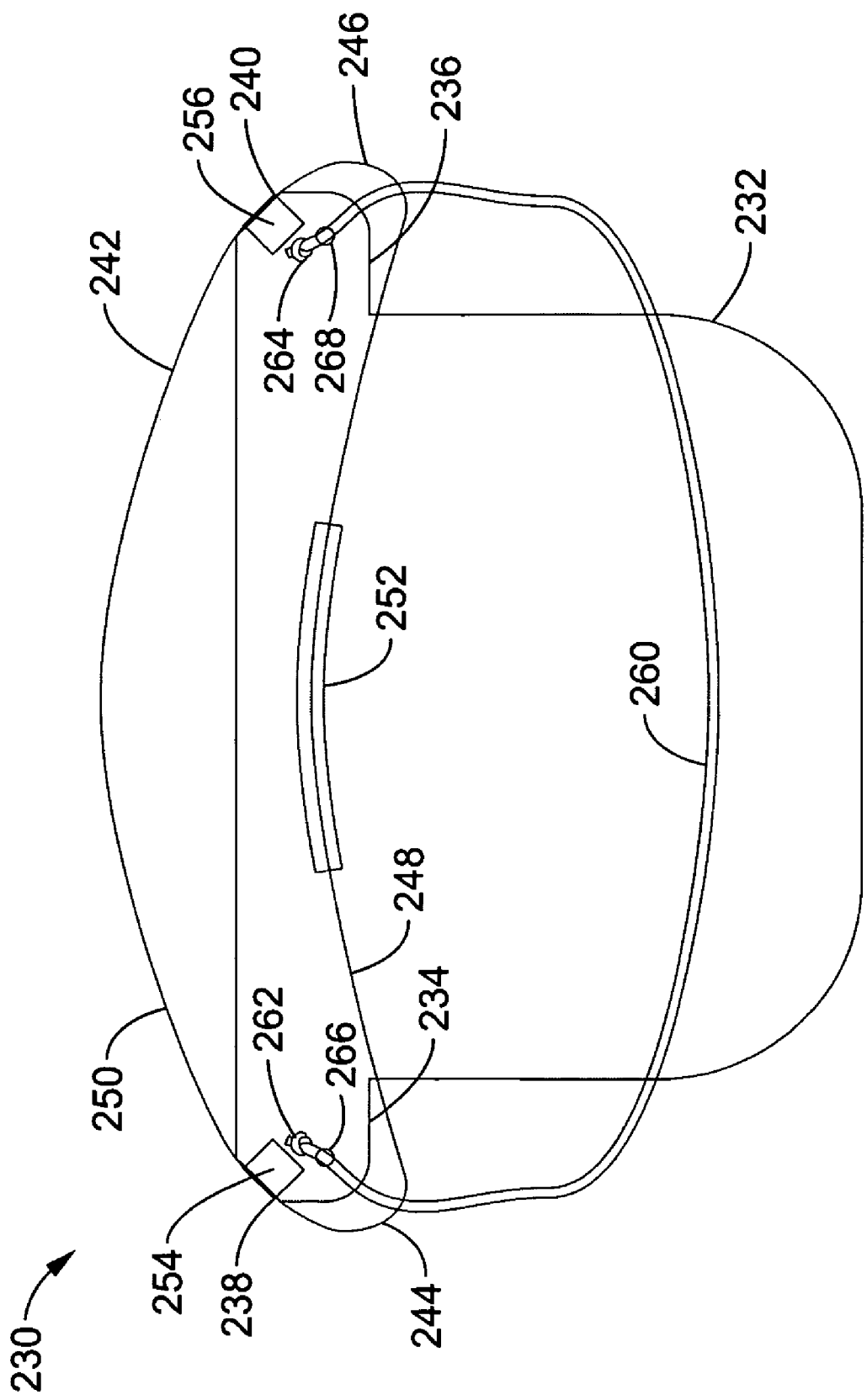
FIG. 26 illustrates a plan view of another embodiment of a ventilated face shield assembly where the glare shield provides the forehead contact point for the face shield assembly.
Figure 27:
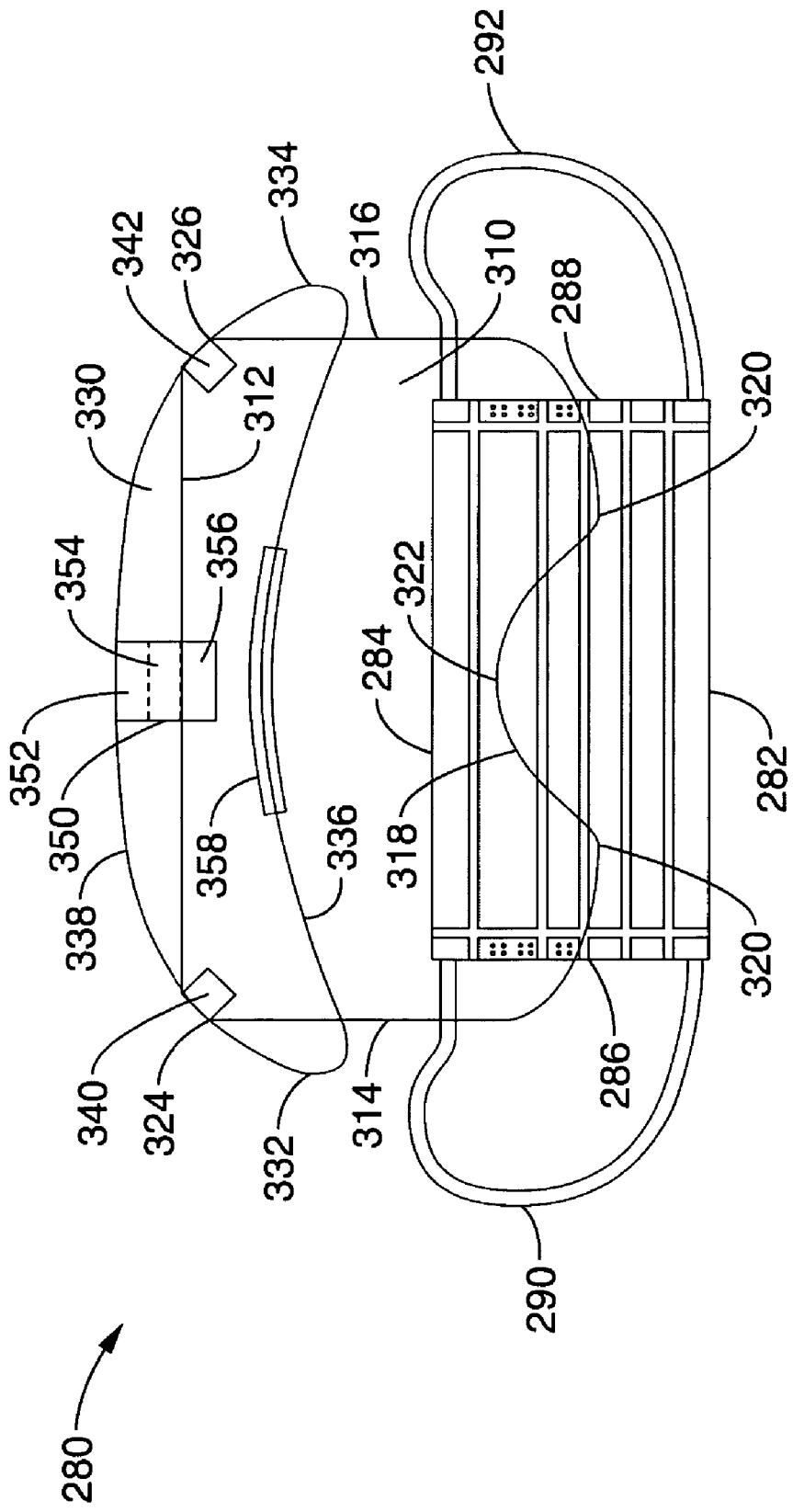
FIG. 27 illustrates a plan view of another embodiment of a ventilated face shield assembly configured with a protective breathing mask and where the glare shield provides the forehead contact point for the face shield assembly.
Figure 28:
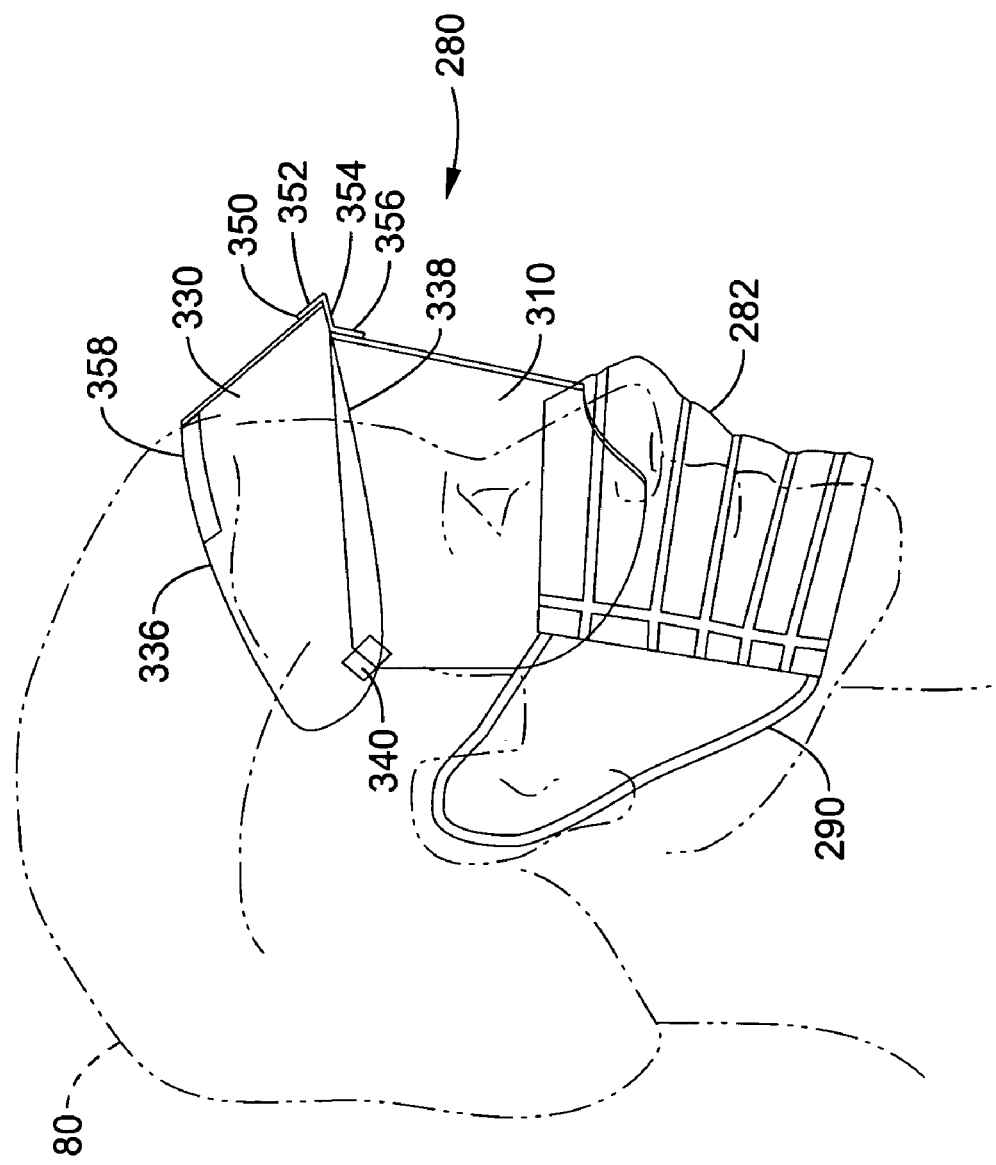
FIG. 28 illustrates a profile view the ventilated face shield assembly shown in FIG. 27 with the loops of the protective breathing mask positioned over the ears of the wearer and the glare shield contacting the forehead of the wearer.

FIG. 26 through FIG. 28 illustrate another embodiment of a ventilated face shield assembly 230 where the glare shield provides the spacing means for the face shield. In FIG. 26, a face shield 232 is cut from a sheet material similar to the face shield in FIG. 1. The top edge of left, right tabs 234, 236 have corners 238, 240 cut off at about 45 degrees. A glare shield 242 is cut from a sheet material in a crescent shape having rounded ends 244, 246 and with the inner and outer edges 248, 250 of the crescent forming about parallel arcuate curves. In a preferred embodiment, the width of the glare shield 242 crescent between the inner and outer edge 248, 250 is about 2½ inches at the widest part and the length of the glare shield from end 244 to end 248 is about 9½ inches. An optional edge cushioning or absorbent material 252 is affixed along inner edge 248 of glare shield 242. Glare shield 242 is laid flat on top of face shield 232 with the outer arcuate edge 250 oriented upward in relation to the top of face shield 232 and the inner surface adjacent to the face shield 232. The outer edge 250 of glare shield 242 near ends 244, 246 is aligned with the 45 degree corners cuts 238, 240 of the tabs 234, 236. Flexible hinges 254, 256 are affixed to the top outer surface of face shield 232, over the 45 degree cuts 238, 240, over the top outer edge 250 of glare shield 242 and affixed to the outer surface of glare shield 242. A cord 260 with ends 262, 264 are threaded under glare shield 250, through apertures 266, 268 in tabs 234, 236 from the inner side and secured with knots or fasteners on the outer side of apertures 266, 268.

When tension is placed on cord 260, face shield 232 will bow outward. Hinges 254, 256 affixed to the outer edge 250 of the glare shield 242 will cause the lower edge 248 of glare shield 242 to rotate upward so glare shield 242 is approximately perpendicular with the bowed face shield 232. When inner edge 248 of glare shield 242 is placed on the forehead of the wearer and cord 260 is looped around the head of the wearer (see FIG. 28) to maintain tension on ends 262, 264 of the cord 260, the glare shield 242 bows slightly until the inner edge 248 conforms to the arcuate shape of the forehead. This forces outer edge 250 of glare shield 242 down and against the top edge of face shield 232 near the center. The placement of the inner edge 248 of glare shield 242 against the forehead and the attached bowed face shield 232 define a space between the face shield and the face of the wearer while the outer edge 250 of the glare shield 242 projects over the top of face shield 232 to provide glare control and protection from objects falling into the ventilated face shield assembly 230. This embodiment has beneficial advantages including material use, assembly, storage, weight and low cost. In a further embodiment, a center flexible hinge (not shown) also couples glare shield 242 to face shield 232. In a preferred embodiment, the ventilated face shield assembly 230 is disposable.

FIG. 27 illustrates another embodiment of a ventilated face shield assembly 280 configured with a protective breathing mask 282. Protective mask 282 is generally rectangular with top edge 284, left right edges 286, 288 and left, right ear loops 300, 302 coupled to left right sides 286, 288. Ear loops 300, 302 could also be ties, bands or other fastening devices for affixing protective mask 282 over the mouth and nose of a wearer. Protective mask 282 could also have a round or oval shape or be contoured to fit over the nose of wearer.

A face shield 310 is cut from a sheet material in a generally rectangular shape and has a straight top edge 312, perpendicular left right edges 314, 316 and a bottom edge 318 having two downward protruding lobes 320 and a centered rounded cutout 322 defining an area where protective mask 282 covers the nose. Corners 324, 326 between top edge 312 and left right sides 314, 316 are cut at about 45 degrees.

A glare shield 330 is cut from a sheet material in a crescent shape having rounded ends 332, 334 and with the inner and outer edges 336, 338 of the crescent forming about parallel arcuate curves. Glare shield 330 is positioned under face shield 310 with outer edge 338 of glare shield 330 near ends 332, 334 aligned with the 45 degree corners cuts 314, 316 of face shield 310. Flexible hinges 340, 342 are affixed to face shield 310 at 45 degree cuts 324, 326, and outer edge 338 of glare shield 330. A center flexible hinge 350 has top section 352 coupled at the top edge 338 of glare shield 330, a middle section 354 and a bottom section 356 coupled near the top edge 312 of face shield 310. In one embodiment, top section 352 of hinge 350 is coupled to the outside of glare shield 330 and bottom section 356 is coupled to the outside of face shield 310. Hinge 350 can also be affixed to the inside of glare shield 330 or the inside of face shield 310.

Protective breathing mask 282 is positioned under face shield 310 and oriented so the lobes 320 on bottom edge 318 are aligned above the horizontal center of protective breathing mask 282. The lower sides of the face shield are affixed to the protective breathing mask 282 along left, right side 286, 288 of breathing mask 282 by spot welding, crimping, adhesive, rivet or other fastening method known in the art. An optional edge cushion 358 is affixed along inner edge 336 of glare shield 330.

FIG. 28 illustrates the ventilated face shield assembly 280 in FIG. 27 with loop 300 of protective breathing mask 282 positioned over the ears of wearer in a conventional manner. As protective breathing mask 282 is positioned to form an arcuate shape to conform to the face of wearer 80, face shield 310 affixed to protective breathing mask 282 bows outward. Outer edge 338 of glare shield 330 rotates outward as described in FIG. 26 but is limited by hinge 350. Inner edge 336 of glare shield 330 rests on the forehead of the wearer. The placement of inner edge 336 against the forehead and the attached bowed face shield 310 define a space 350 between face shield 310 and the face of the wearer 80 while outer edge 338 of the glare shield 330 projects over the top of face shield 310 to provide glare control and protection from objects falling into the ventilated face shield assembly 280. Glare shield 330 can be perforated or have other ventilation apertures. In other embodiments, ventilated face shield assembly 280 can be configured to fit with military helmets or other protective head gear.

An embodiment of the present invention has been depicted by way of example, with a few contemplated variations and options. It should be appreciated, however, that elements of the invention such as the shape or structure of the face shield, glare shield, ventilated spacer, retainer and so forth, may be implemented in a number of alternative ways by one of ordinary skill in the art without departing from the teachings of the present invention.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for protecting the face of a wearer and controlling glare comprising:

a face shield having a planar configuration and an arcuate configuration;

a glare shield coupled to said face shield;

said glare shield having a planar configuration and an arcuate configuration;

means for fastening adapted to couple said face shield in said arcuate configuration to said glare shield in said arcuate configuration; and means for spacing coupled to said face shield;

wherein said means for spacing is adapted to position said face shield to protect the face of the wearer when said face shield is in said arcuate configuration;

wherein said glare shield in said arcuate configuration is adapted to control glare when fastened to said face shield by said fastening means;

wherein said face shield and said glare shield are adapted for flat storage when in their respective planar configurations; and wherein said means for spacing comprises a flexible headband having ventilation apertures.

2. An apparatus as recited in claim 1, wherein said face shield material is selected from the group consisting of polystyrene, acrylic, acetate, polyethylene, terephthalate, and polycarbonate.

3. An apparatus as recited in claim 1, wherein said glare shield material is selected from the group consisting of polystyrene, acrylic, acetate, polyethylene, terephthalate, and polycarbonate.

4. An apparatus as recited in claim 1, wherein said glare shield comprises a material through which light transmission is limited.

5. An apparatus as recited in claim 1, wherein said means for fastening comprises:
a plurality of flexible hinges coupling said face shield to said glare shield; and
a flexible cord having first, second ends;
wherein said first, second ends are configured to couple said face shield in said arcuate configuration to said glare shield in said arcuate configuration when said cord is placed in a tension state.

6. An apparatus as recited in claim 1, further comprising:
means for retaining coupled to said face shield;
wherein said means for retaining is adapted to maintain said face shield in said arcuate configuration; and
wherein said means for retaining is further adapted to maintain said face shield in position to protect the face of the wearer.

7. An apparatus as recited in claim 6, wherein said means for retaining comprises:
a flexible cord having first, second ends;
wherein said first, second ends are configured to couple said face shield in said arcuate configuration to said glare shield in said arcuate configuration when said cord is placed in a tension state; and
wherein flexible headband maintains said face shield in position to protect the face of the wearer when said cord is placed in a tension state.

8. An apparatus as recited in claim 7 wherein said flexible headband has a compressed state adapted for flat storage.

9. An apparatus as recited in claim 7, wherein said flexible headband comprises:
a flexible headband having alternating slits;
wherein said headband is expanded lengthwise prior to coupling to said face shield; and
wherein expansion of said head band forms triangular ventilation spaces at said slits.

10. An apparatus as recited in claim 7, wherein said flexible headband comprises:
a strip of flexible material having first and second ends;
first and second apertures positioned at said first, second ends;
said first and second apertures adapted to cooperate with said two ends of said cord;
wherein said strip is adapted to position said face shield to protect the face of the wearer when tension is placed on said cord.

11. An apparatus as recited in claim 1, wherein said means for fastening comprises a plurality of flexible hinges coupling said glare shield to said face shield.

12. An apparatus as recited in claim 7, wherein said means for retaining further comprises:
a cord keeper adapted to couple to said flexible cord at said first, second ends of said flexible cord;
said cord keeper comprising first and second mating hollow hemispheres;
said first hemisphere having a bridge, said bridge positioned across the diameter of said first hemisphere;
said second hemisphere hingedly coupled to said first hemisphere;
said second hemisphere having a pair of barbed ridges, said barbed ridges oriented parallel to said bridge;
said barbed ridges protruding outside of said second hemisphere;
said barbed ridges adapted to grasp said bridge when said first and second hemispheres are mated;
wherein when said cord is positioned perpendicular on said bridge, and said second hemisphere is mated with said first hemisphere, said cord is secured between said bridge and said barbed ridges; and
said first hemisphere is secured to said second hemisphere by said barbed ridges grasping said cord on said bridge.

13. An apparatus as recited in claim 6, wherein said means for retaining comprises:
a protective breathing mask, said breathing mask coupled to said face shield;
said protective breathing mask further comprising a pair of ear loops;
wherein said face shield is maintained in an arcuate configuration when tension is place on said ear loops; and
wherein said face shield is positioned to protect the face of the wearer when said ear loops are positioned on the ears of the wearer.

14. An apparatus as recited in claim 1, comprising:
a protective breathing mask, said breathing mask coupled to said face shield;
said protective breathing mask comprising a pair of ear loops;
wherein said face shield is maintained in an arcuate configuration when tension is place on said ear loops; and
wherein said face shield is positioned to protect the face of the wearer when said ear loops are positioned on the ears of the wearer.

15. An apparatus as recited in claim 1, wherein said face shield and said glare shield are cut from a single sheet of material with the connection therebetween comprising a hinge.

16. An apparatus for protecting the face of a wearer and controlling glare, comprising:
a face shield having a planar configuration and an arcuate configuration;
a glare shield coupled to said face shield;
said glare shield having a planar configuration and an arcuate configuration;
a fastener adapted to couple said face shield in said arcuate configuration to said glare shield in said arcuate configuration; and
a spacer coupled to said face shield;
wherein said spacer comprises a flexible headband having ventilation apertures and coupled to said face shield;
wherein said spacer is adapted to position said face shield to protect the face of the wearer when said face shield is in said arcuate configuration;
wherein said glare shield in said arcuate configuration is adapted to control glare when fastened to said face shield by said fastener; and
wherein said face shield and said glare shield are adapted for flat storage when in their respective planar configurations.

17. An apparatus as recited in claim 16, wherein said spacer comprises said glare shield in said arcuate position when coupled to said face shield by said fastening means.

18. An apparatus as recited in claim 16, wherein said face shield and said glare shield are cut from a single sheet of material with the connection therebetween comprising a hinge.

19. An apparatus as recited in claim 16, wherein said fastener comprises:
a plurality of flexible hinges coupling said face shield to said glare shield; and
a flexible cord having first and second ends;
wherein said first, second ends are configured to couple said face shield in said arcuate configuration to said glare shield in said arcuate configuration when said cord is placed in a tension state.

20. An apparatus as recited in claim 16, further comprising:
a retainer coupled to said face shield;
wherein said retainer is adapted to maintain said face shield in said arcuate configuration; and
wherein said retainer is further adapted to maintain said face shield in position to protect the face of the wearer.

21. An apparatus as recited in claim 20, said retainer comprising:
a flexible cord having first, second ends;
wherein said first, second ends are configured to couple said face shield in said arcuate configuration to said glare shield in said arcuate configuration when said cord is placed in a tension state; and
wherein said spacer maintains said face shield in position to protect the face of the wearer when said cord is placed in a tension state.

22. An apparatus as recited in claim 21, wherein said spacer comprises:
a flexible headband having alternating slits;
wherein said headband is expanded lengthwise prior to coupling to said face shield; and
wherein expansion of said head band forms triangular ventilation spaces at said slits.

23. An apparatus as recited in claim 21, wherein said spacer comprises:
a strip of flexible material having first and second ends;
first and second apertures positioned at said first, second ends;
said first and second apertures adapted to cooperate with said two ends of said cord;
wherein said strip is adapted to position said face shield to protect the face of the wearer when tension is placed on said cord.

24. An apparatus as recited in claim 21, wherein said spacer comprises said glare shield in said arcuate position when coupled to said face shield by said fastener.

25. An apparatus as recited in claim 24, wherein said fastener comprises a plurality of flexible hinges coupling said glare shield to said face shield.

26. An apparatus as recited in claim 21, wherein said retainer further comprises:
a cord keeper adapted to couple to said flexible cord at said first, second ends of said flexible cord;
said cord keeper comprising first and second mating hollow hemispheres;
said first hemisphere having a bridge, said bridge positioned across the diameter of said first hemisphere;
said second hemisphere hingedly coupled to said first hemisphere;
said second hemisphere having a pair of barbed ridges, said barbed ridges oriented parallel to said bridge;
said barbed ridges protruding outside of said second hemisphere;
said barbed ridges adapted to grasp said bridge when said first and second hemispheres are mated;
wherein when said cord is positioned perpendicular on said bridge, and said second hemisphere is mated with said first hemisphere, said cord is secured between said bridge and said barbed ridges; and
said first hemisphere is secured to said second hemisphere by said barbed ridges grasping said cord on said bridge.

27. An apparatus as recited in claim 20, wherein said retainer comprises:
a protective breathing mask, said breathing mask coupled to said face shield;
said protective breathing mask further comprising a pair of ear loops;
wherein said face shield is maintained in an arcuate configuration when tension is place on said ear loops; and
wherein said face shield is positioned to protect the face of the wearer when said ear loops are positioned on the ears of the wearer.

28. An apparatus as recited in claim 16, further comprising:
a protective breathing mask, said breathing mask coupled to said face shield;
said protective breathing mask further comprising a pair of ear loops;
wherein said face shield is maintained in an arcuate configuration when tension is place on said ear loops; and
wherein said face shield is positioned to protect the face of the wearer when said ear loops are positioned on the ears of the wearer.

29. An apparatus as recited in claim 28:
wherein said spacer comprises said glare shield in said arcuate configuration; and
wherein said fastener comprises a plurality of hinges coupling said glare shield to said face shield.

30. An apparatus for protecting the face of a wearer and controlling glare comprising:
a face shield having a planar configuration and an arcuate configuration;
a glare shield coupled to said face shield;
said glare shield having a planar configuration and an arcuate configuration;
means for fastening adapted to couple said face shield in said arcuate configuration to said glare shield in said arcuate configuration;
means for spacing coupled to said face shield;
wherein said means for spacing is adapted to position said face shield to protect the face of the wearer when said face shield is in said arcuate configuration;
wherein said glare shield in said arcuate configuration is adapted to control glare when fastened to said face shield by said fastening means;
wherein said face shield and said glare shield are adapted for flat storage when in their respective planar configurations;
means for retaining coupled to said face shield;
wherein said means for retaining is adapted to maintain said face shield in said arcuate configuration;
wherein said means for retaining is further adapted to maintain said face shield in position to protect the face of the wearer;
wherein said means for retaining comprises:
a flexible cord having first, second ends;
wherein said first, second ends are configured to couple said face shield in said arcuate configuration to said glare shield in said arcuate configuration when said cord is placed in a tension state;
wherein said means for spacing maintains said face shield in position to protect the face of the wearer when said cord is placed in a tension state;
wherein said means for spacing comprises:
a flexible headband having alternating slits;
wherein said headband is expanded lengthwise prior to coupling to said face shield;
wherein expansion of said head band forms triangular ventilation spaces at said slits.

31. An apparatus for protecting the face of a wearer and controlling glare comprising:
a face shield having a planar configuration and an arcuate configuration;
a glare shield coupled to said face shield;

said glare shield having a planar configuration and an arcuate configuration;
means for fastening adapted to couple said face shield in said arcuate configuration to said glare shield in said arcuate configuration;
means for spacing coupled to said face shield;
wherein said means for spacing is adapted to position said face shield to protect the face of the wearer when said face shield is in said arcuate configuration;
wherein said glare shield in said arcuate configuration is adapted to control glare when fastened to said face shield by said fastening means;
wherein said face shield and said glare shield are adapted for flat storage when in their respective planar configurations;
means for retaining coupled to said face shield;
wherein said means for retaining is adapted to maintain said face shield in said arcuate configuration;
wherein said means for retaining is further adapted to maintain said face shield in position to protect the face of the wearer;
wherein said means for retaining comprises:
a flexible cord having first, second ends;
wherein said first, second ends are configured to couple said face shield in said arcuate configuration to said glare shield in said arcuate configuration when said cord is placed in a tension state;
wherein said means for spacing maintains said face shield in position to protect the face of the wearer when said cord is placed in a tension state;
wherein said means for spacing comprises:
a strip of flexible material having first and second ends;
first and second apertures positioned at said first, second ends;
said first and second apertures adapted to cooperate with said two ends of said cord;
wherein said strip is adapted to position said face shield to protect the face of the wearer when tension is placed on said cord.

32. An apparatus for protecting the face of a wearer and controlling glare comprising:
a face shield having a planar configuration and an arcuate configuration;
a glare shield coupled to said face shield;
said glare shield having a planar configuration and an arcuate configuration;
means for fastening adapted to couple said face shield in said arcuate configuration to said glare shield in said arcuate configuration;
means for spacing coupled to said face shield;
wherein said means for spacing is adapted to position said face shield to protect the face of the wearer when said face shield is in said arcuate configuration;
wherein said glare shield in said arcuate configuration is adapted to control glare when fastened to said face shield by said fastening means;
wherein said face shield and said glare shield are adapted for flat storage when in their respective planar configurations;
means for retaining coupled to said face shield;
wherein said means for retaining is adapted to maintain said face shield in said arcuate configuration;
wherein said means for retaining is further adapted to maintain said face shield in position to protect the face of the wearer;
wherein said means for retaining comprises:
a flexible cord having first, second ends;
wherein said first, second ends are configured to couple said face shield in said arcuate configuration to said glare shield in said arcuate configuration when said cord is placed in a tension state;
wherein said means for spacing maintains said face shield in position to protect the face of the wearer when said cord is placed in a tension state;
a cord keeper adapted to couple to said flexible cord at said first, second ends of said flexible cord;
said cord keeper comprising first and second mating hollow hemispheres;
said first hemisphere having a bridge, said bridge positioned across the diameter of said first hemisphere;
said second hemisphere hingedly coupled to said first hemisphere;
said second hemisphere having a pair of barbed ridges, said barbed ridges oriented parallel to said bridge;
said barbed ridges protruding outside of said second hemisphere;
said barbed ridges adapted to grasp said bridge when said first and second hemispheres are mated;
wherein when said cord is positioned perpendicular on said bridge, and said second hemisphere is mated with said first hemisphere, said cord is secured between said bridge and said barbed ridges; and
said first hemisphere is secured to said second hemisphere by said barbed ridges grasping said cord on said bridge.

33. An apparatus for protecting the face of a wearer and controlling glare, comprising:
a face shield having a planar configuration and an arcuate configuration;
a glare shield coupled to said face shield;
said glare shield having a planar configuration and an arcuate configuration;
a fastener adapted to couple said face shield in said arcuate configuration to said glare shield in said arcuate configuration;
a spacer coupled to said face shield;
wherein said spacer is adapted to position said face shield to protect the face of the wearer when said face shield is in said arcuate configuration;
wherein said glare shield in said arcuate configuration is adapted to control glare when fastened to said face shield by said fastener;
wherein said face shield and said glare shield are adapted for flat storage when in their respective planar configurations;
a retainer coupled to said face shield;
wherein said retainer is adapted to maintain said face shield in said arcuate configuration;
wherein said retainer is further adapted to maintain said face shield in position to protect the face of the wearer;
wherein said retainer comprises:
a flexible cord having first, second ends;
wherein said first, second ends are configured to couple said face shield in said arcuate configuration to said glare shield in said arcuate configuration when said cord is placed in a tension state;
wherein said spacer maintains said face shield in position to protect the face of the wearer when said cord is placed in a tension state;
wherein said spacer comprises a flexible headband having ventilation apertures.

34. An apparatus as recited in claim 33, wherein said flexible headband has a compressed state adapted for flat storage.

35. An apparatus for protecting the face of a wearer and controlling glare, comprising:
- a face shield having a planar configuration and an arcuate configuration;
- a glare shield coupled to said face shield;
- said glare shield having a planar configuration and an arcuate configuration;
- a fastener adapted to couple said face shield in said arcuate configuration to said glare shield in said arcuate configuration;
- a spacer coupled to said face shield;
- wherein said spacer is adapted to position said face shield to protect the face of the wearer when said face shield is in said arcuate configuration;
- wherein said glare shield in said arcuate configuration is adapted to control glare when fastened to said face shield by said fastener;
- wherein said face shield and said glare shield are adapted for flat storage when in their respective planar configurations;
- a retainer coupled to said face shield;
- wherein said retainer is adapted to maintain said face shield in said arcuate configuration;
- wherein said retainer is further adapted to maintain said face shield in position to protect the face of the wearer;
- wherein said retainer comprises:
  - a flexible cord having first, second ends;
  - wherein said first, second ends are configured to couple said face shield in said arcuate configuration to said glare shield in said arcuate configuration when said cord is placed in a tension state;
  - wherein said spacer maintains said face shield in position to protect the face of the wearer when said cord is placed in a tension state;
- wherein said spacer comprises:
  - a flexible headband having alternating slits;
  - wherein said headband is expanded lengthwise prior to coupling to said face shield;
  - wherein expansion of said head band forms triangular ventilation spaces at said slits.

36. An apparatus for protecting the face of a wearer and controlling glare, comprising:
- a face shield having a planar configuration and an arcuate configuration;
- a glare shield coupled to said face shield;
- said glare shield having a planar configuration and an arcuate configuration;
- a fastener adapted to couple said face shield in said arcuate configuration to said glare shield in said arcuate configuration;
- a spacer coupled to said face shield;
- wherein said spacer is adapted to position said face shield to protect the face of the wearer when said face shield is in said arcuate configuration;
- wherein said glare shield in said arcuate configuration is adapted to control glare when fastened to said face shield by said fastener;
- wherein said face shield and said glare shield are adapted for flat storage when in their respective planar configurations;
- a retainer coupled to said face shield;
- wherein said retainer is adapted to maintain said face shield in said arcuate configuration;
- wherein said retainer is further adapted to maintain said face shield in position to protect the face of the wearer;
- wherein said retainer comprises:
  - a flexible cord having first, second ends;
  - wherein said first, second ends are configured to couple said face shield in said arcuate configuration to said glare shield in said arcuate configuration when said cord is placed in a tension state;
  - wherein said spacer maintains said face shield in position to protect the face of the wearer when said cord is placed in a tension state;
- wherein said spacer comprises:
  - a strip of flexible material having first and second ends;
  - first and second apertures positioned at said first, second ends;
  - said first and second apertures adapted to cooperate with said two ends of said cord;
  - wherein said strip is adapted to position said face shield to protect the face of the wearer when tension is placed on said cord.

37. An apparatus for protecting the face of a wearer and controlling glare, comprising:
- a face shield having a planar configuration and an arcuate configuration;
- a glare shield coupled to said face shield;
- said glare shield having a planar configuration and an arcuate configuration;
- a fastener adapted to couple said face shield in said arcuate configuration to said glare shield in said arcuate configuration;
- a spacer coupled to said face shield;
- wherein said spacer is adapted to position said face shield to protect the face of the wearer when said face shield is in said arcuate configuration;
- wherein said glare shield in said arcuate configuration is adapted to control glare when fastened to said face shield by said fastener;
- wherein said face shield and said glare shield are adapted for flat storage when in their respective planar configurations;
- a retainer coupled to said face shield;
- wherein said retainer is adapted to maintain said face shield in said arcuate configuration;
- wherein said retainer is further adapted to maintain said face shield in position to protect the face of the wearer;
- wherein said retainer comprises:
  - a flexible cord having first, second ends;
  - wherein said first, second ends are configured to couple said face shield in said arcuate configuration to said glare shield in said arcuate configuration when said cord is placed in a tension state;
  - wherein said spacer maintains said face shield in position to protect the face of the wearer when said cord is placed in a tension state;
  - a cord keeper adapted to couple to said flexible cord at said first, second ends of said flexible cord;
  - said cord keeper comprising first and second mating hollow hemispheres;
  - said first hemisphere having a bridge, said bridge positioned across the diameter of said first hemisphere;
  - said second hemisphere hingedly coupled to said first hemisphere;
  - said second hemisphere having a pair of barbed ridges, said barbed ridges oriented parallel to said bridge;

said barbed ridges protruding outside of said second hemisphere;

said barbed ridges adapted to grasp said bridge when said first and second hemispheres are mated;

wherein when said cord is positioned perpendicular on said bridge, and said second hemisphere is mated with said first hemisphere, said cord is secured between said bridge and said barbed ridges; and said first hemisphere is secured to said second hemisphere by said barbed ridges grasping said cord on said bridge.

* * * * *